US012125196B2

(12) United States Patent
Kawabata

(10) Patent No.: US 12,125,196 B2
(45) Date of Patent: Oct. 22, 2024

(54) COMPUTER PROGRAM, PROCESSOR FOR ENDOSCOPE, AND INFORMATION PROCESSING METHOD

(71) Applicant: HOYA CORPORATION, Tokyo (JP)

(72) Inventor: Yuichi Kawabata, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 544 days.

(21) Appl. No.: 17/420,454

(22) PCT Filed: Aug. 2, 2019

(86) PCT No.: PCT/JP2019/030488
§ 371 (c)(1),
(2) Date: Jul. 2, 2021

(87) PCT Pub. No.: WO2021/024301
PCT Pub. Date: Feb. 11, 2021

(65) Prior Publication Data
US 2022/0084194 A1    Mar. 17, 2022

(51) Int. Cl.
*G06T 7/00* (2017.01)
*A61B 1/00* (2006.01)
*A61B 1/045* (2006.01)

(52) U.S. Cl.
CPC ........ *G06T 7/0012* (2013.01); *A61B 1/00004* (2013.01); *A61B 1/0005* (2013.01); *A61B 1/045* (2013.01); *G06T 2207/10068* (2013.01); *G06T 2207/20081* (2013.01); *G06T 2207/20084* (2013.01); *G06T 2207/30004* (2013.01)

(58) Field of Classification Search
CPC ........................ A61B 1/0005; G06T 7/0012
See application file for complete search history.

(56) References Cited

U.S. PATENT DOCUMENTS

| 7,566,301 B2 | 7/2009 | Negishi | |
|---|---|---|---|
| 2012/0078045 A1* | 3/2012 | Sasaki | A61B 1/00009 600/109 |
| 2015/0320514 A1* | 11/2015 | Ahn | A61B 34/30 606/130 |
| 2016/0206283 A1* | 7/2016 | Ota | A61B 8/467 |
| 2017/0071504 A1 | 3/2017 | Wang | |

(Continued)

FOREIGN PATENT DOCUMENTS

| JP | 2007-014452 | 1/2007 |
|---|---|---|
| JP | 2017-055954 | 3/2017 |

(Continued)

OTHER PUBLICATIONS

Official Communication issued in International Bureau of WIPO Patent Application No. PCT/JP2019/030488, dated Oct. 1, 2019.

*Primary Examiner* — Di Xiao
(74) *Attorney, Agent, or Firm* — GREENBLUM & BERNSTEIN, P.L.C.

(57) ABSTRACT

A computer program causes a computer to execute processing for acquiring examination point information regarding an examination point included in an examination target portion using an endoscope, acquiring an endoscopic image captured by the endoscope, determining whether the endoscope has reached the examination point on the basis of image analysis of the acquired endoscopic image, and outputting a notification in a case where the endoscope has reached the examination point.

18 Claims, 20 Drawing Sheets

(56) References Cited

U.S. PATENT DOCUMENTS

| | | | |
|---|---|---|---|
| 2017/0105609 A1* | 4/2017 | Nakayama | A61B 1/00009 |
| 2017/0126786 A1* | 5/2017 | Satkunarajah | G06F 3/04842 |
| 2018/0242818 A1* | 8/2018 | Kubo | A61B 1/005 |
| 2018/0253839 A1* | 9/2018 | Zur | A61B 1/000094 |
| 2019/0213185 A1* | 7/2019 | Arroyo | G06F 16/2428 |
| 2019/0231444 A1 | 8/2019 | Tojo et al. | |
| 2020/0090548 A1* | 3/2020 | Kimura | G06T 7/00 |
| 2020/0352411 A1* | 11/2020 | Tojo | A61B 1/0051 |
| 2024/0016366 A1* | 1/2024 | Jeong | G06T 7/0012 |

FOREIGN PATENT DOCUMENTS

| | | |
|---|---|---|
| JP | 2017-108792 | 6/2017 |
| WO | 2018/069992 | 4/2018 |
| WO | 2018/211674 | 11/2018 |

\* cited by examiner

FIG. 3

| EXAMINER ID | NAME | SKILL LEVEL | NUMBER OF EXAMINATIONS | EXAMINATION HISTORY |
|---|---|---|---|---|
| 01002··· | *** | 4 | 40 | *** |
| 01003··· | *** | 2 | 20 | *** |
| ⋮ | | | | |

EXAMINATION POINT DB ~233

EXAMINATION POINT INFORMATION ~234

| EXAMINATION POINT ID | CHECK POINT | EXAMINATION POINT POSITION | IMAGE | ENDOSCOPE TYPE | NOTIFICATION | TARGET SKILL LEVEL |
|---|---|---|---|---|---|---|
| 0101 | 01 | *** | *** | UPPER PORTION (DIGESTIVE ORGAN) | YES | 5, 4, 3, 2, 1 |
| 0102 | 011 | *** | *** | UPPER PORTION (DIGESTIVE ORGAN) | NO | 5, 4, 3, 2, 1 |
| 0201 | 02 | *** | *** | UPPER PORTION (DIGESTIVE ORGAN) | YES | 4, 3, 2, 1 |
| ... | ... | | | | | |
| 5201 | 52 | *** | *** | LOWER PORTION (DIGESTIVE ORGAN) | YES | 3, 2, 1 |
| ... | ... | | | | | |

CANDIDATE INFORMATION ~235

| ENDOSCOPE TYPE | EXAMINATION POINT ID (CANDIDATE INFORMATION) | | | | | |
|---|---|---|---|---|---|---|
| UPPER PORTION (DIGESTIVE ORGAN) | 0101 | 0102 | 0103 | ... | 0201 | 0202 |
| UPPER PORTION (RESPIRATORY ORGAN) | 1101 | 1102 | 1103 | ... | 1201 | 1202 |
| ... | | | ... | | | |
| LOWER PORTION (DIGESTIVE ORGAN) | 5101 | 5102 | 5103 | ... | 5201 | 5202 |
| ... | | | ... | | | |

FIG. 7

| ENDOSCOPE TYPE | CANDIDATE CHECK POINT | | | | | |
|---|---|---|---|---|---|---|
| UPPER PORTION (DIGESTIVE ORGAN) | 01 | 02 | 03 | 04 | 05 | 06 |

⇩ RECEIVE SELECTION ⇩

| ENDOSCOPE TYPE | SELECTION CHECK POINT | | | | | |
|---|---|---|---|---|---|---|
| UPPER PORTION (DIGESTIVE ORGAN) | — | 02 | — | 04 | 05 | — |

⇩ DETERMINE EXAMINATION POINT ⇩

EXAMINATION No. ***

| ENDOSCOPE TYPE | EXAMINATION POINT ID | | | | |
|---|---|---|---|---|---|
| UPPER PORTION (DIGESTIVE ORGAN) | 0101 | 0102 | 0103 | 0201 | 0202 |

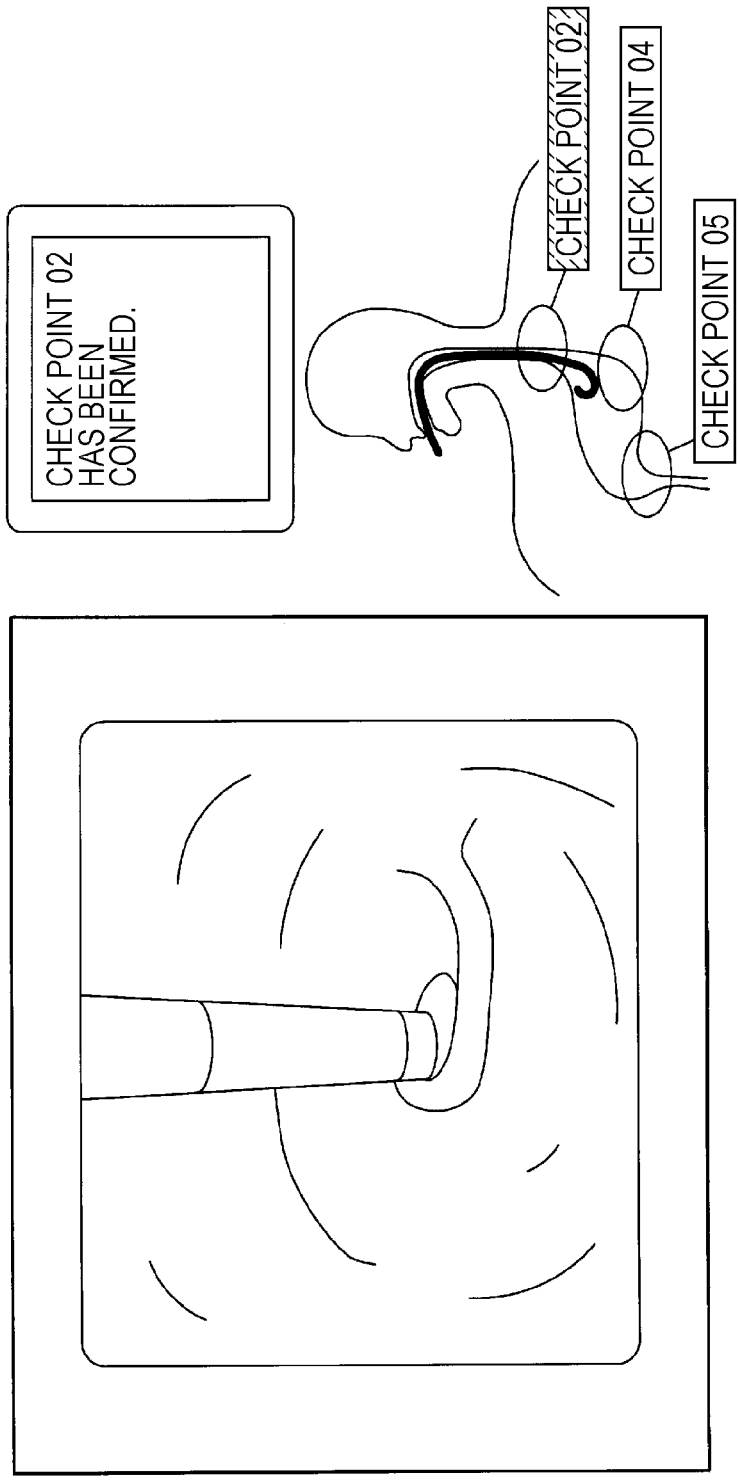

FIG. 15

| MOTION INFORMATION ID | ENDOSCOPE TYPE | SKILL LEVEL | MOTION INFORMATION |
|---|---|---|---|
| 1001··· | UPPER PORTION (DIGESTIVE ORGAN) | 5 | *** |
| 1001··· | UPPER PORTION (DIGESTIVE ORGAN) | 4 | *** |
| ⋮ | | ⋮ | |
| 5010··· | UPPER PORTION (RESPIRATORY ORGAN) | 3 | *** |
| ⋮ | | | |

COMPUTER PROGRAM, PROCESSOR FOR ENDOSCOPE, AND INFORMATION PROCESSING METHOD

TECHNICAL FIELD

The present technology relates to a computer program, a processor for an endoscope, and an information processing method.

BACKGROUND ART

In the case of performing an endoscopic examination, one or a plurality of examination target portions are determined in advance for each patient who is a subject, and the examination target portions are imaged in a body cavity of the patient according to a prescribed procedure to perform image diagnosis. Specifically, a person in charge of examination of the endoscope inserts the endoscope insertion portion into the body cavity of the patient, and causes the endoscope insertion portion to reach a predetermined examination target portion while confirming the position of the distal end of the insertion portion of the endoscope in the body cavity. Then, while an image is confirmed on the monitor screen each time it arrives, a still image is photographed by pressing a button for still image photographing while finely adjusting a photographing position and a direction.

The number of captured images may be several to 20 or more in one medical examination, and it is desired to examine a large number of people in a short time at a medical site. Therefore, the person in charge of examination is required to perform an accurate and rapid imaging operation. Under such a situation, particularly an error such as failure in imaging of a part of the examination portion is likely to occur, and if failure in imaging occurs at a necessary examination portion, accurate diagnosis becomes difficult. In addition, in order to obtain a missed image, a burden on the patient is increased in order to re-take the image with the endoscope by re-examination.

In a medical facility, it is effective to define an examination protocol defining an examination procedure and the like in order to prevent a difference in a burden on a patient and an organ observation method from being generated due to a difference in experience and skill of a person in charge of examination. Patent Literature 1 discloses an endoscope operation support system that can easily confirm whether an examination has been performed according to an examination protocol in a medical facility that defines the examination protocol.

CITATION LIST

PATENT LITERATURE

Patent Literature 1: JP 2017-108792 A

SUMMARY OF INVENTION

Technical Problem

However, in the endoscope business support system of Patent Literature 1, the confirmation as to whether the examination has been performed is performed after the examination based on the examination record. Therefore, there is a concern about omission of the observation content. In order to perform an appropriate examination content regardless of the experience and skill of a person in charge of examination, it is desirable to derive information regarding the examination contents in real time.

An object of the present disclosure is to provide a computer program or the like that realizes efficient derivation of information regarding an examination content.

Solution to Problem

A computer program according to an aspect of the present disclosure causes a computer to execute acquiring examination point information regarding an examination point included in an examination target portion using an endoscope, acquiring an endoscopic image captured by the endoscope, determining whether the endoscope has reached the examination point on the basis of image analysis of the acquired endoscopic image, and outputting a notification when the endoscope has reached the examination point.

Advantageous Effects of Invention

According to the present disclosure, it is possible to provide a computer program or the like that realizes efficient derivation of information regarding an examination content.

BRIEF DESCRIPTION OF DRAWINGS

FIG. 3 is a diagram illustrating a content example of information stored in an examiner DB.

FIG. 4 is a diagram illustrating a content example of information stored in an examination point DB.

FIG. 7 is an explanatory diagram for explaining a flow of setting examination point information.

FIG. 9 is a schematic diagram illustrating an example of a notification screen for displaying notification information.

FIG. 15 is a diagram illustrating a content example of information stored in an action learning DB.

DESCRIPTION OF EMBODIMENTS

The present invention will be specifically described with reference to the drawings illustrating embodiments of the invention.

First Embodiment

Figure 1:
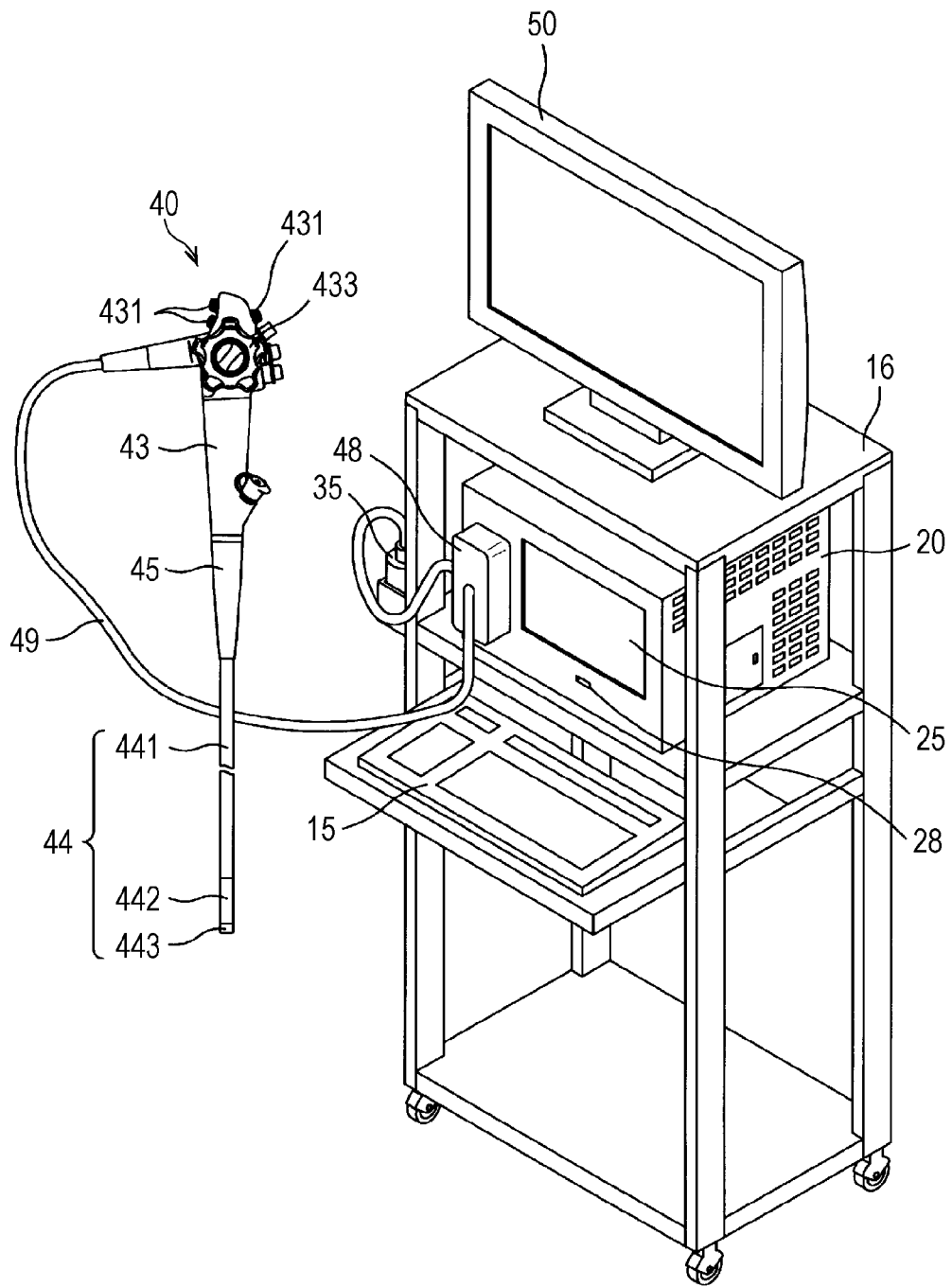
FIG. 1 is an explanatory diagram illustrating the appearance of a diagnostic support system.

FIG. 1 is an explanatory diagram illustrating the appearance of a diagnostic support system 100. The diagnostic support system 100 includes an endoscope processor 20, an endoscope 40, and a display device 50. The display device 50 is, for example, a liquid crystal display device or an organic EL (Electro Luminescence) display device.

The display device 50 is installed on the upper stage of a storage shelf 16 with casters. The endoscope processor 20 is housed in the middle stage of the storage shelf 16. The storage shelf 16 is arranged in the vicinity of an endoscopic examination bed (not illustrated). The storage shelf 16 includes a pull-out shelf on which a keyboard 15 connected to the endoscope processor 20 is mounted.

The endoscope processor 20 has a substantially rectangular parallelepiped shape and is provided with a touch panel 25 on one surface. A reading unit 28 is arranged at the bottom of the touch panel 25. The reading unit 28 is a connection interface for reading and writing a portable recording medium such as a USB connector, an SD (Secure Digital) card slot, or a CD-ROM (Compact Disc Read Only Memory) drive.

The endoscope 40 includes an insertion portion 44, an operation unit 43, a light guide flexible tube 49, and a scope connector 48. The operation unit 43 is provided with a control button 431. The insertion portion 44 is long, and has one end connected to the operation unit 43 via a bend preventing portion 45. The insertion portion 44 includes a soft portion 441, a bending portion 442, and a distal tip 443 in the order from the operation unit 43 side. The bending portion 442 is bent according to an operation of a bending knob 433. Physical detection devices such as a three-axis acceleration sensor, a gyro sensor, a geomagnetic sensor, or a magnetic coil sensor may be mounted on the insertion portion 44, and when the endoscope 40 is inserted into the body of the subject, detection results from these physical detection devices may be acquired.

The light guide flexible tube 49 is long, and has a first end connected to the operation unit 43 and a second end connected to the scope connector 48. The light guide flexible tube 49 is flexible. The scope connector 48 has a substantially rectangular parallelepiped shape. The scope connector 48 is provided with an air/water supply port 36 (see FIG. 2) for connecting an air/water supply tube.

In the diagnostic support system 100, the endoscope processor 20 determines the examination content of the endoscope 40 in real time based on an endoscopic image 59 captured by the endoscope 40, and notifies the examiner of the determination result. The examiner operates the endoscope 40 while referring to the notification.

Figure 2:
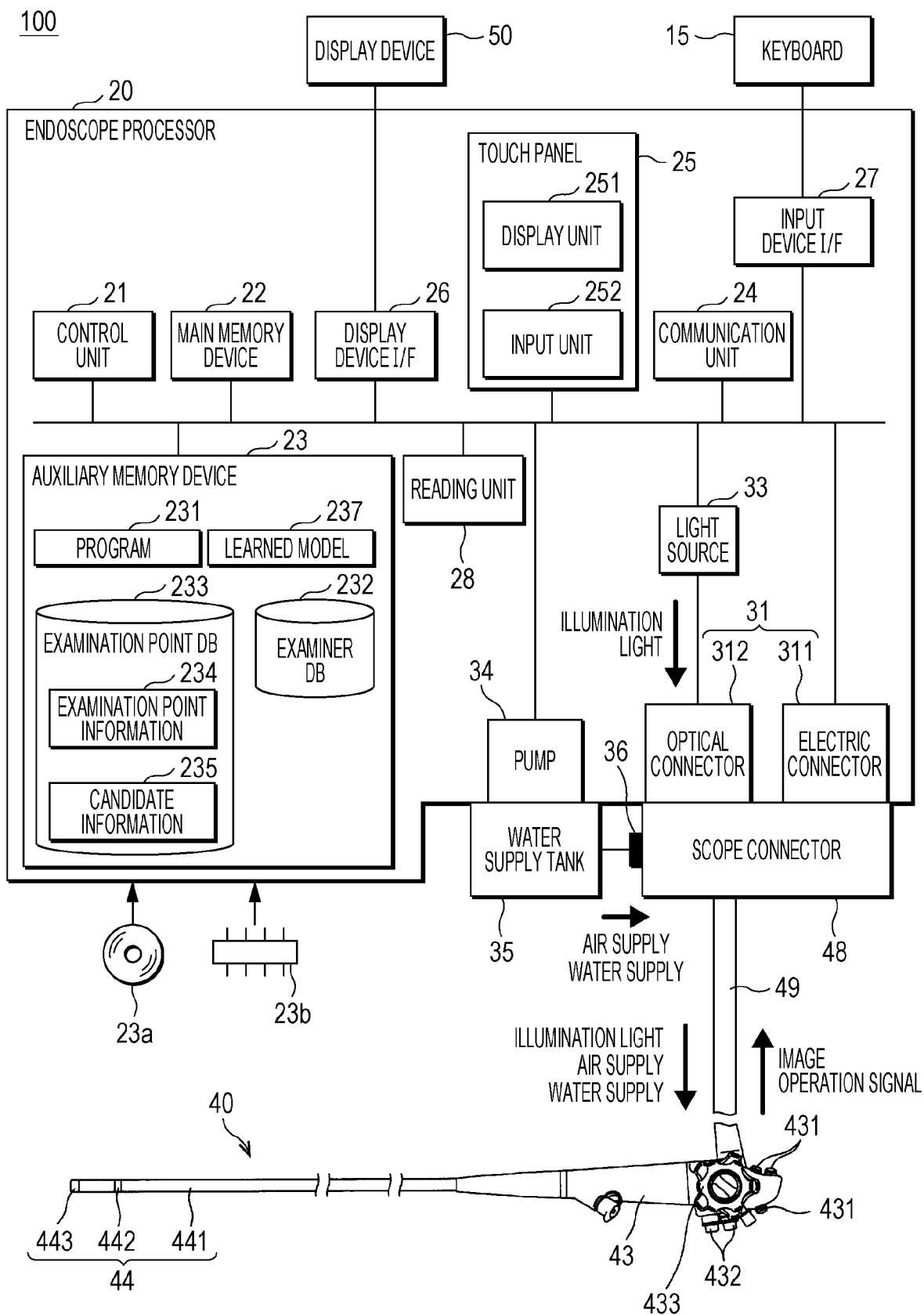
FIG. 2 is an explanatory diagram for explaining a configuration of a diagnostic support system according to a first embodiment.

FIG. 2 is an explanatory diagram for explaining a configuration of the diagnostic support system 100 according to a first embodiment. As described above, the diagnostic support system 100 includes the endoscope processor 20, the endoscope 40, and the display device 50. In addition to the touch panel 25 and the reading unit 28, the endoscope processor 20 includes a control unit 21, a main memory device 22, an auxiliary memory device 23, a communication unit 24, a display device I/F (Interface) 26, and an input device I/F 27, an endoscope connector 31, a light source 33, a pump 34, and a bus. The endoscope connector 31 includes an electric connector 311 and an optical connector 312.

The control unit 21 is an arithmetic control device that executes a program 231 of this embodiment. For the control unit 21, one or a plurality of central processing units (CPUs), micro-processing units (MPUs), graphics processing units (GPUs), or the like is used. The control unit 21 is connected to each hardware unit constituting the endoscope processor 20 via the bus.

The main memory device 22 is a memory device such as a static random access memory (SRAM), a dynamic random access memory (DRAM), and a flash memory. The main memory device 22 temporarily holds information necessary during the processing performed by the control unit 21 and a program being executed by the control unit 21.

The auxiliary memory device 23 is a memory device such as an SRAM, a flash memory, or a hard disk. The auxiliary memory device 23 holds the program 231 executed by the control unit 21, a learned model 237, and various data necessary for executing the program 231. The program 231 and the learned model 237 may be downloaded from an external device via a network such as a so-called Internet via the communication unit 24 and stored in the auxiliary memory device 23 by the control unit 21. The program 231 and the learned model 237 may be read by the control unit 21 from a portable storage medium 23a via the reading unit 28 and stored in the auxiliary memory device 23. The program 231 and the learned model 237 may be read from a semiconductor memory 23b by the control unit 21.

The auxiliary memory device 23 stores an examiner DB (Database) 232 and an examination point DB 233. The examiner DB 232 and the examination point DB 233 may be stored in an external mass storage device connected to the endoscope processor 20.

The communication unit 24 is an interface for data communication between the endoscope processor 20 and the network. The touch panel 25 includes a display unit 251 such as a liquid crystal display panel, and an input unit 252 layered on the display unit 251.

The display device I/F 26 is an interface for connecting the endoscope processor 20 and the display device 50. The input device I/F 27 is an interface for connecting the endoscope processor 20 and an input device such as the keyboard 15.

The light source 33 is, for example, a high-luminance white light source such as a white LED. The light source 33 is connected to the bus via a driver (not illustrated). The on/off of the light source 33 and the change of brightness are controlled by the control unit 21. The illumination light emitted from the light source 33 is incident on the optical connector 312. The optical connector 312 engages with the scope connector 48 to supply illumination light to the endoscope 40.

The pump 34 generates pressure for the air supply/water supply function of the endoscope 40. The pump 34 is connected to the bus via a driver (not illustrated). The on/off and pressure change of the pump 34 are controlled by the control unit 21. The pump 34 is connected to the air/water supply port 36 provided in the scope connector 48 via a water supply tank 35.

The function of the endoscope 40 connected to the endoscope processor 20 will be outlined. A fiber bundle, a cable bundle, an air supply tube, a water supply tube, and the like are inserted inside the scope connector 48, the light guide flexible tube 49, the operation unit 43, and the insertion portion 44. The illumination light emitted from the light source 33 is radiated from an illumination window provided at the distal tip 443 via the optical connector 312 and the fiber bundle.

The range illuminated by the illumination light is captured by an image sensor provided at the distal tip 443. The captured image is transmitted from the image sensor to the endoscope processor 20 via the cable bundle and the electric connector 311.

The control unit 21 performs image processing on the captured image to generate the endoscopic image 59 that makes it easy for the examiner performing examination to visually find a lesion. The control unit 21 outputs the endoscopic image 59 to the display device 50. The examiner operates the endoscope 40 while confirming the endoscopic image 59, and when reaching a predetermined examination point, presses a button for still image shooting to shoot a still image.

FIG. 3 is a diagram illustrating a content example of information stored in the examiner DB 232. The examiner DB 232 stores an attribute such as a name of an examiner and information regarding an examination history of the examiner in association with an examiner ID for identifying the examiner. The information regarding the examination history of the examiner includes the skill level of the examiner, the number of examinations, the examination history, and the like. The skill level is information indicating a skill level of the examiner with respect to the endoscopic examination. For example, the skill level is indicated in five stages of 1 to 5, and the higher the numerical value, the more skilled in the endoscopic examination. The number of examinations is the number of endoscopic examinations performed by the examiner so far. The examination history is an execution history of the endoscopic examination performed by the examiner so far, and may include an execution date, an examination content, a log of an operation signal at the time of examination, and the like. Note that FIG. 3 is an example, and the content stored in the examiner DB 232 is not limited.

FIG. 4 is a diagram illustrating a content example of information stored in the examination point DB 233. The control unit 21 acquires various types of information regarding the examination point included in an examination target portion in advance and stores the information in the examination point DB 233. The examination point is a portion to be examined when the endoscope moves in the body in the examination using the endoscope, and is an examination portion serving as a determination point of the examination content. The examination point includes a portion around the check point, a specific point between check points, and the like in addition to the examination portion serving as a so-called check point. The diagnostic support system 100 determines the examination content of the endoscope 40 in real time based on the analysis result of the image of the endoscopic image 59 and the examination point image of examination point information 234, and outputs a notification corresponding to the determination result to the examiner. The examination point DB 233 stores the examination point information 234 and candidate information 235.

The examination point information 234 stores check point information, an examination point position, an examination point image, an endoscope type, and notification information in association with an examination point ID for identifying the examination point information. The check point information includes information of a check point related to the examination point, and for example, information of an adjacent check point of the examination point is stored. When the examination point is a check point, a check point number displayed on the display device 50 may be included. The examination point position may include, for example, information related to the position of the examination point, such as position information in the body of the examination point, distance information between the examination points, and the like. The examination point image may include a plurality of pieces of image information indicating the examination point. The endoscope type may include a type of the endoscope 40 connected to the endoscope processor 20. In the examination using the endoscope, the endoscope 40 of a type suitable for the examination target portion is selected and used. As the endoscope type, for example, an upper portion (digestive organ), an upper portion (respiratory organ), a lower portion (digestive organ), and the like are stored. The notification information may include information regarding whether a notification is output at the examination point. In the examination point for which the output of notification is stored, a notification for notifying the examiner of the examination content is output. The notification information may store the presence or absence of notification in association with the skill level.

Further, the examination point information 234 may store the target skill level in association with the examination point ID. The target skill level includes information on the skill level of the examiner to examine the examination point associated with the target skill level. The target skill level will be described in detail in other embodiments.

In the endoscopic examination, a guideline (manual) for allowing the examiner of various skill levels to photograph images all over the inside of the gastrointestinal tract at an appropriate level is defined (see, for example, "Manual of Gastroendoscopic Examination for Countermeasure Screening, 2015 Edition (pages 56 to 63)"). The examination point position may be set based on these guidelines. For example, in the case of performing a gastroscopic examination, the examination point position to be photographed includes the photographing place described in the manual of gastroendoscopic examination.

The candidate information 235 stores the candidate information of the examination point in association with the endoscope type which is information for identifying the type of the endoscope. The candidate information includes information related to a candidate of an examination point to be a determination point of an examination content in a case where a predetermined type of endoscope is used. The candidate information may include the order of passage of the examination points at the time of examination. In the example of FIG. 4, the candidate information is stored as the examination point ID. Note that FIG. 4 is an example, and the content stored in the examination point DB 233 is not limited.

Figure 5:
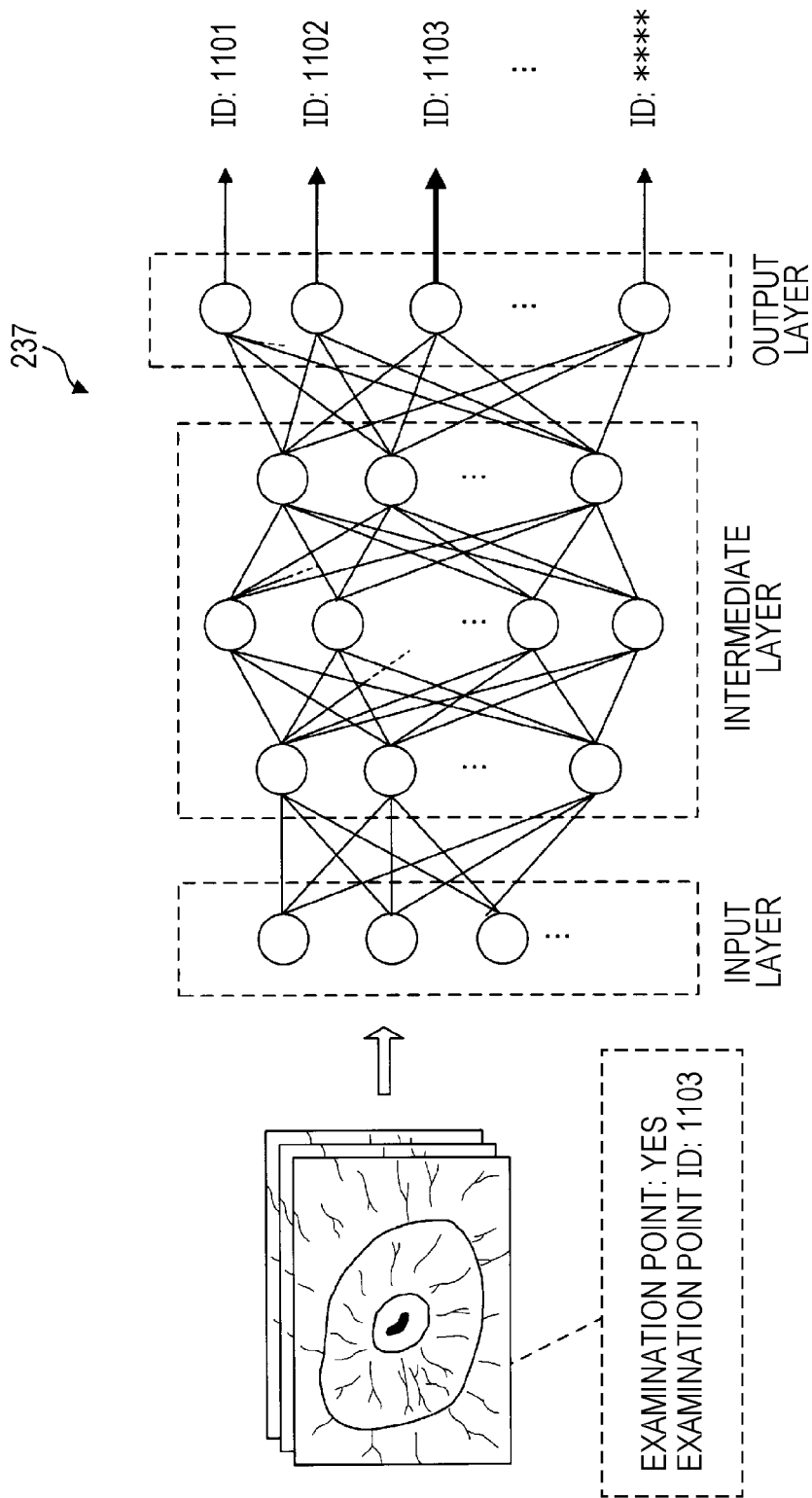
FIG. 5 is an explanatory diagram regarding generation processing of a learned model.

FIG. 5 is an explanatory diagram regarding generation processing of the learned model 237. The control unit 21 constructs (generates) a learned model of machine learning including deep learning in which the endoscopic image 59 is input and the examination point information corresponding to the endoscopic image 59 is output. In this embodiment, the examination point ID is output from the output layer as the examination point information. The control unit 21 performs machine learning for learning an image feature amount regarding an examination point in the endoscopic image 59. The learned model 237 is, for example, a neural network, which is a convolution neural network (CNN). The learned model 237 includes an input layer that receives an input of the endoscopic image 59, an output layer that outputs an examination point ID corresponding to the endoscopic image 59, and an intermediate layer that extracts an image feature amount of the endoscopic image 59.

A neural network (learned model 237) learned using training data is assumed to be used as a program module that is a part of artificial intelligence software. The learned model 237 is used by the endoscope processor 20 including the control unit 21 (CPU or the like) and the auxiliary memory device 23 as described above, and is executed by the endoscope processor 20 having the arithmetic processing capability in this manner, thereby constituting a neural network system. That is, the control unit 21 of the endoscope processor 20 operates to perform calculation of extracting the feature amount of the endoscopic image input to the input layer according to the command from the learned model 237 stored in the auxiliary memory device 23, and output the examination point ID corresponding to the endoscopic image from the output layer.

The input layer has a plurality of neurons that receive an input of the pixel value of each pixel included in the endoscopic image 59, and passes the input pixel value to the intermediate layer. The intermediate layer includes a plurality of neurons that extract the image feature amount of the endoscopic image 59, and passes the image feature amount extracted using various parameters to the output layer. For example, when the learned model 237 is a CNN, the intermediate layer has a configuration in which a convolution layer that convolutes a pixel value of each pixel input from the input layer and a pooling layer that maps a pixel value convoluted by the convolution layer are alternately connected. The intermediate layer finally extracts the image feature amount while compressing the pixel information of the image region of the object.

The output layer includes a plurality of neurons that output the examination point ID corresponding to the endoscopic image. Each neuron can be divided in association with each examination point ID. The output value from the output layer can be interpreted as a probability that the examination point ID classified into each classification is included in the endoscopic image. For example, among the neurons with the examination point IDs of 1030, 1130, 2012, . . . , the information on the examination point ID of the neuron with the highest probability or the neuron with the probability equal to or greater than a threshold can be set as the output value of the learned model 237. The output layer outputs an output value based on the image feature amount output from the intermediate layer.

The control unit 21 learns various parameters in the intermediate layer by using training data in which a plurality of endoscopic images obtained by photographing the examination point by the endoscope and the examination point ID in each endoscopic image are associated with each other. For example, as illustrated in FIG. 5, the training data is constructed as a data set in which the presence or absence of the examination point and the examination point ID are labeled with respect to the endoscopic image. The control unit 21 performs learning using a large amount of data of endoscopic images collected in examinations performed in the past. The data may include an endoscopic image in a state in which the examination point is not included.

The control unit 21 inputs the endoscopic image included in the training data to the input layer, performs arithmetic processing in the intermediate layer, and acquires the examination point ID from the output layer. The control unit 21 compares the examination point ID output from the output layer with the examination point ID labeled with respect to the image in the training data, that is, the correct value, and optimizes various parameters used for the arithmetic processing in the intermediate layer such that the output value from the output layer approaches the correct value. The parameter is, for example, a weight, a bias, or the like between neurons. The method of optimizing various parameters is not particularly limited, but for example, the control unit 21 optimizes various parameters using an error back propagation method. The control unit 21 performs the above processing on each endoscopic image included in the training data, and generates the learned model 237.

Although the description has been given assuming that the learned model 237 is the CNN in this embodiment, the learned model 237 is not limited to the CNN. When the time-series data is acquired, a neural network other than the CNN, for example, a recurrent neural network (RNN) or a long short term memory (LSTM) network may be used. Further, it may be a learned model constructed by another learning algorithm such as a reinforcement learning model, a support vector machine, or a regression tree that does not use a neural network.

Figure 6:
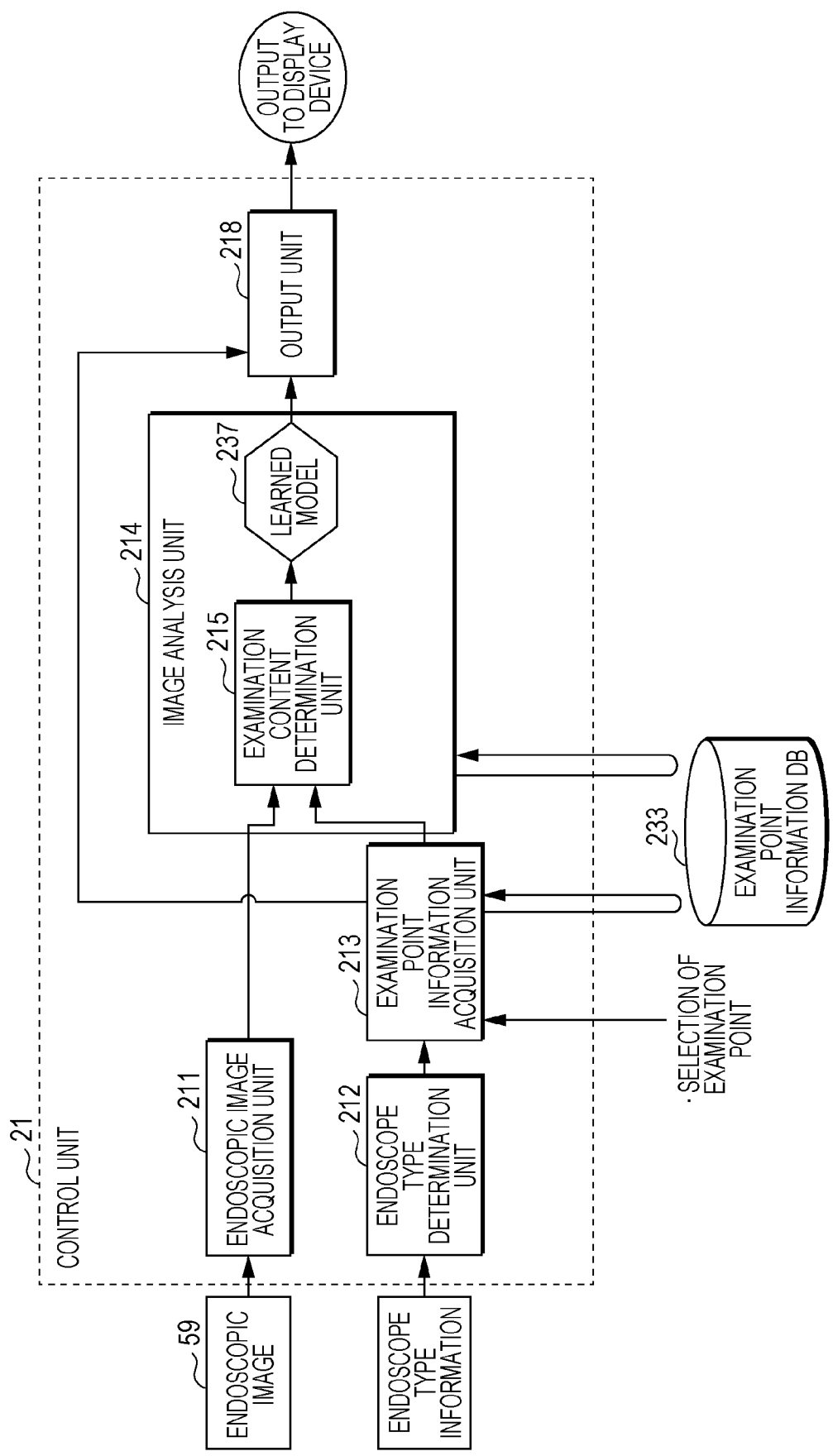
FIG. 6 is a functional block diagram illustrating functional units included in a control unit.

FIG. 6 is a functional block diagram illustrating functional units included in the control unit 21. The control unit 21 implements the functions of an endoscopic image acquisition unit 211, an endoscope type determination unit 212, an examination point information acquisition unit 213, an image analysis unit 214, and an output unit 218 by executing the program 231 stored in the auxiliary memory device 23. In FIG. 6, these parts are shown as functional units. The control unit 21 functions as the learned model 237 by executing the program 231 stored in the auxiliary memory device 23 or reading the entity file constituting the learned model 237.

The endoscopic image acquisition unit 211 acquires the endoscopic image 59. The control unit 21 acquires a captured image taken by an image sensor provided at the distal tip 443 of the endoscope 40. The captured image is obtained as a moving image, and is constituted by still images of a plurality of frames such as 60 frames per second, for example. The control unit 21 performs various types of image processing such as gamma correction, white balance correction, and shading correction on the captured image, generates the endoscopic image 59 in a state in which the user can easily view the endoscopic image, and stores the endoscopic image in the auxiliary memory device 23. The endoscopic image acquisition unit 211 acquires the generated endoscopic image 59. Note that the endoscopic image 59 input to the endoscopic image acquisition unit 211 may be a captured image at a stage where various types of image processing are not performed, or may be an image in the middle stage of generating the endoscopic image 59 from the captured image. The acquired endoscopic image 59 is input to the image analysis unit 214.

The endoscope type determination unit 212 acquires endoscope type information based on the information acquired from the endoscope 40. The endoscope type information is information related to the type of the endoscope 40 connected to the endoscope processor 20. The endoscope type determination unit 212 determines the type of the endoscope 40 from a connector shape of the endoscope 40 connected to the endoscope processor 20, signal information obtained from the endoscope 40, or the like, and acquires endoscope type information. The acquired endoscope type information is input to the examination point information acquisition unit 213.

The examination point information acquisition unit 213 refers to the examination point DB 233 and acquires candidate information including the examination point corresponding to the endoscope type information. In addition, the examination point information acquisition unit 213 receives the examination point ID of the check point selected by the examiner, and derives the examination point information based on the candidate information and the check point selected by the examiner.

FIG. 7 is an explanatory diagram for explaining a flow of setting of examination point information. The examination point information acquisition unit 213 reads the candidate information corresponding to the acquired endoscope type information from the examination point DB 233, and displays the examination point which is the check point included in the candidate information on the display device 50 via the output unit 218 (see FIG. 8). The examination point is displayed by, for example, a check point number. The examiner selects or adds a check point from among candidate check points displayed on the display device 50 according to an examination purpose or the like.

The examination point information acquisition unit 213 receives an input of the keyboard 15, the mouse, or the like, and acquires the examination point ID of the selected check point. The examination point information acquisition unit 213 refers to the examination point DB 233 and specifies the examination point related to the check point based on the selected check point. The examination point includes a selected check point, a passing point related to each check point, and the like. The examination point information acquisition unit 213 derives the examination point information associated with these examination points from the examination point DB 233. The examination point information acquisition unit 213 temporarily stores the derived examination point information in the auxiliary memory device 23. The examination point information is input to the image analysis unit 214. Note that these input operations and output operations may be performed using the display unit 251 and the input unit 252 of the touch panel 25.

The image analysis unit 214 includes an examination content determination unit (determination unit) 215. The examination content determination unit 215 performs image analysis of the endoscopic image 59 and determines examination point information corresponding to the endoscope 40. The examination content determination unit 215 provides the endoscopic image 59 to the learned model 237 as input information. The learned model 237 outputs the examination point ID included in the endoscopic image as output information according to the endoscopic image 59. The examination content determination unit 215 determines whether the endoscope 40 has reached the examination point on the basis of whether the examination point ID output from the learned model 237 matches the examination point ID included in the examination point information derived by the examination point information acquisition unit 213, that is, the examination point ID included in the examination target portion.

The examination content determination unit 215 determines whether an appropriate examination content has been performed using the endoscope 40. When the endoscope 40 has reached a check point, the examination content determination unit 215 determines whether an appropriate examination content has been performed at the check point. The execution of an appropriate examination content means that, for example, at a check point, the control button 431 is pressed and a capture operation of a predetermined image is performed. The examination content determination unit 215 determines whether a capture operation has been performed at a check point on the basis of operation information of the endoscope 40, capture history information of an image, or the like. Note that the examination content is not limited to the image capture operation, and may be, for example, air supply or water supply operation, removal of a foreign object, or the like. In addition, the examination content determination unit 215 determines the presence or absence of omission of passage through the examination point based on the history of reaching the examination point. The examination content determination unit 215 acquires information of a plurality of examination points to be detected by the endoscope 40 in advance as the examination point information. The examination point information includes information such as a passage order and a position of the examination point. In a case where the examination point is not detected from the endoscopic image 59 in a predetermined order in the middle of the examination, the examination content determination unit 215 determines that a predetermined examination point to pass through is omitted. The examination content determination unit 215 creates notification information according to the determination result. The notification information of the determination result is input to the output unit 218.

The examination content determination unit 215 may acquire the position information in the body of the distal tip 443 of the endoscope 40 at the time of determining the examination content. It is possible to obtain a more accurate determination result by determining whether the endoscope 40 has reached the examination point on the basis of the position information of the distal tip 443 and the image analysis result. Although there are various methods of detecting the position information of the distal tip 443, for example, the examination content determination unit 215 may detect the position information on the basis of the insertion amount of the endoscope 40. The insertion amount of the insertion portion 44 into the body is detected by comparison with the reference point with reference to the previous insertion. The examination content determination unit 215 derives the position information of the distal tip 443 from the insertion amount of the endoscope 40 based on attributes such as the height and weight of the subject acquired in advance. Note that, in this case, a plurality of coils is arranged inside the insertion portion 44, an electric signal generated by the coils is output to the outside via the lead wire by receiving an electromagnetic wave from the outside, and the shape of the endoscope 40 may be grasped based on the amplitude, phase, and the like of the output electric signal. By detecting the shape of the endoscope 40 in the body and correcting the position information on the basis of the insertion amount of the endoscope 40 including rotation, curvature, and the like, accurate position information of the endoscope 40 in the body can be obtained. For example, based on the position information and the image analysis result, the examination content determination unit 215 determines that the examination content at the examination point is omitted when the examination point is not detected when the predetermined position is passed.

In addition, the examination content determination unit 215 may arrange a sensor that detects position information on the distal tip 443 and derive the position information of the distal tip 443 from the detection information of the sensor. For example, the examination content determination unit 215 acquires signals indicating the measurement information of the acceleration and the rotation angular velocity output from a three-axis acceleration sensor and a gyro sensor disposed in the distal tip 443, and derives the position information of the distal tip 443 from the acquired detection result of the sensor.

Note that the method of image analysis is not limited to using the learned model 237, and other known methods may be used. For example, the examination content determination unit 215 may determine whether the examination point is included in the endoscopic image 59 on the basis of the feature amount of the endoscopic image 59 and the feature amount of the examination point stored in advance using a method such as pattern matching.

The output unit 218 creates display screen information based on various types of information such as candidate information and notification information of a determination result, and outputs the created display screen information to the display device 50.

In this embodiment, the sharing of each functional unit in the series of processing is an example, and the present invention is not limited thereto. The function of each functional unit including the learned model 237 may be realized by a control unit (not illustrated) of an external server communicatively connected to the endoscope processor 20. Further, the control unit 21 of the endoscope processor 20 and the control unit of the external server may function as each functional unit in a series of processing in cooperation by performing inter-process communication, for example.

Figure 8A:
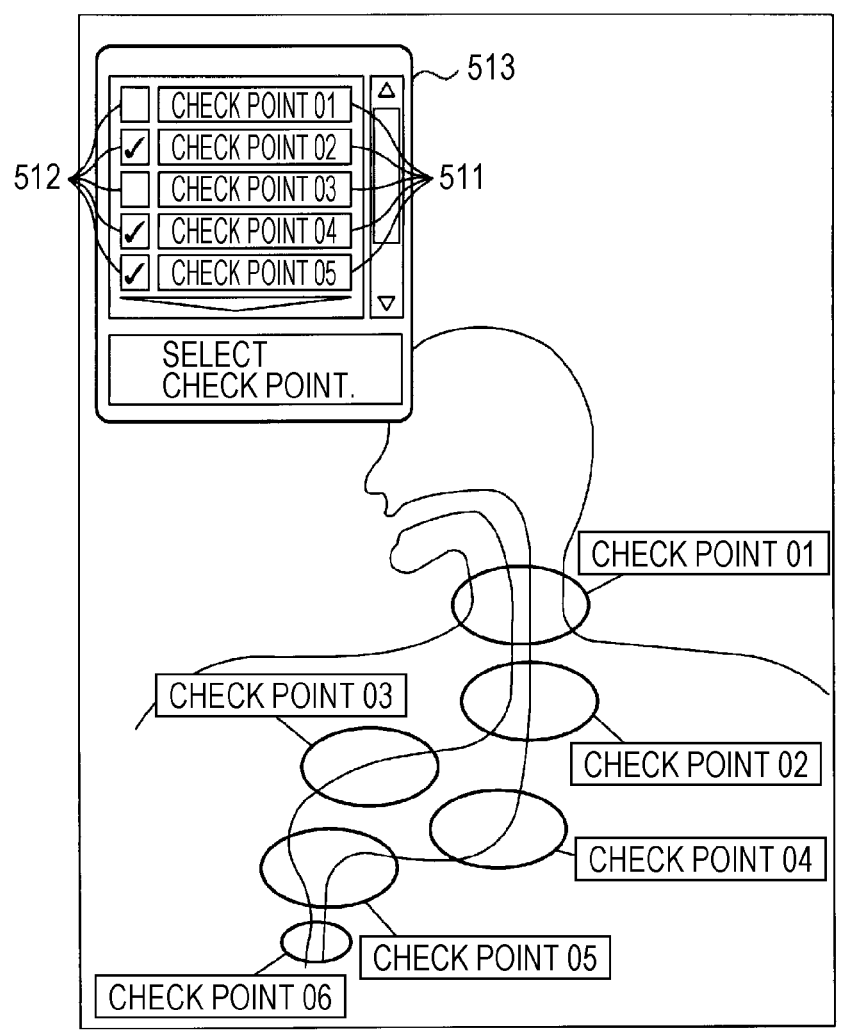
FIG. 8A is a schematic diagram illustrating an example of a check point input screen.
Figure 8B:
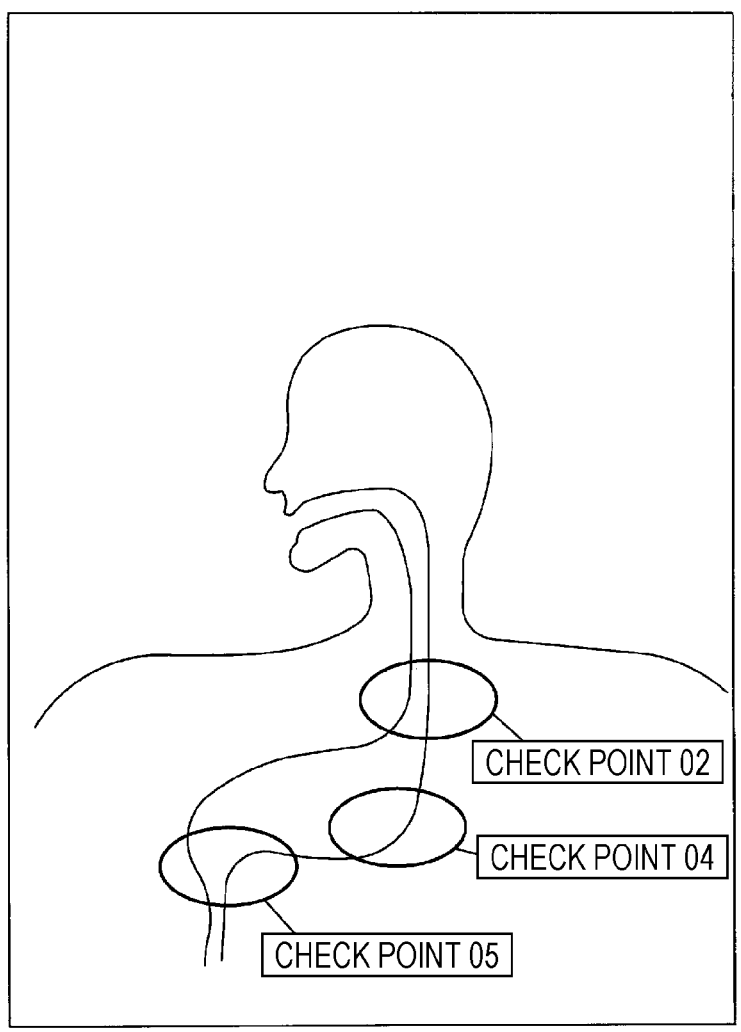
FIG. 8B is a schematic diagram illustrating an example of a check point input screen.

FIGS. 8A and 8B are schematic diagrams illustrating an example of a check point input screen. FIG. 8A illustrates an example of an input screen for receiving input of selection information. The input screen includes a candidate information field 511 indicating candidate information of the examination point and a selection acceptance field 512 for accepting the selection of the examiner from the candidates of the examination point. In the example of FIG. 8A, the input screen includes an illustration of a human body including an examination target portion for performing an endoscopic examination, and the candidate information is displayed using a check point (examination point) number and a circle indicating a corresponding position in the body. Further, the input screen includes an input box 513 including the candidate information field 511 indicated by a plurality of check point numbers and a check box of the selection acceptance field 512 that accepts a selection operation of the examiner associated with each check point number. The examiner performs a selection operation of a check box of a desired check point from the check point candidates and sets the selected check point.

The control unit 21 refers to the examination point DB 233 and specifies a plurality of candidate check points included in the candidate information based on the endoscope type information. The control unit 21 creates display screen information including candidate check points and displays the display screen information on the display device 50 as illustrated in FIG. 8A. In FIG. 8A, the control unit 21 receives an input operation of the examination point ID of the selected check point through the keyboard 15, the mouse, or the like. The control unit 21 creates screen information based on the examination point ID of the selected check point which has been acquired, and displays the screen information on the display device 50 as illustrated in FIG. 8B. On the screen, only the check point selected by the examiner is displayed together with a circle indicating the examination position, and is superimposed and displayed on the illustration of the human body.

Figure 10:
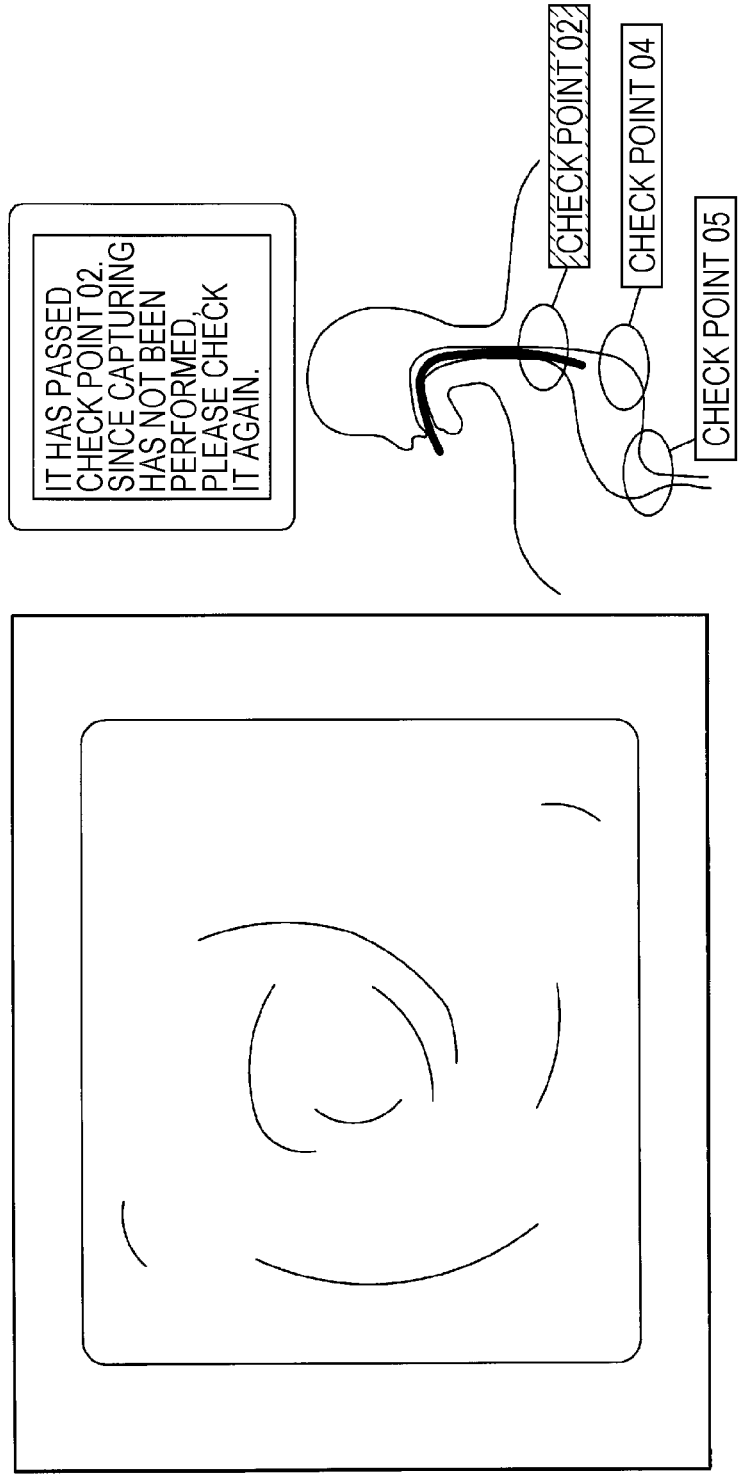
FIG. 10 is a schematic diagram illustrating an example of a notification screen displaying notification information.
Figure 11:
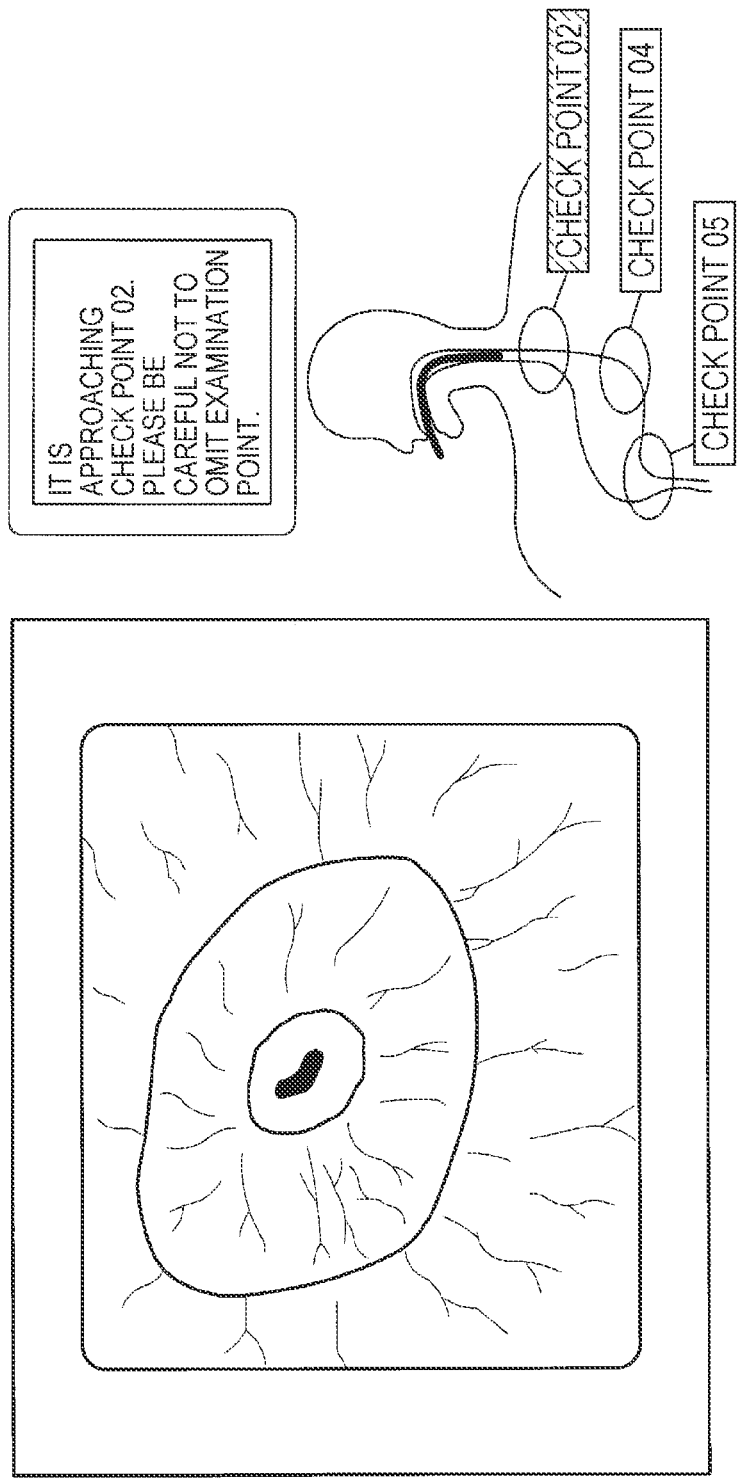
FIG. 11 is a schematic diagram illustrating an example of a notification screen displaying notification information.

FIGS. 9 to 11 are schematic diagrams illustrating an example of a notification screen for displaying notification information. The notification information is displayed in parallel with the endoscopic image 59 on a part of the display screen of the display device 50, for example. FIG. 9 illustrates an example of a notification screen for notifying that the examination content has been performed. The notification screen includes a text box including notification information and information of an illustration indicating the current position of the endoscope 40 in the body. When it is determined that an appropriate examination content has been performed at the set examination point, a notification indicating confirmation completion is displayed to the examiner. The notification screen includes a text indicating notification contents, such as "Check point 02 has been confirmed". The control unit 21 performs determination based on the endoscopic image 59 and the examination point information, and acquires a determination result regarding implementation of examination content at a predetermined examination point. A notification DB (not illustrated) of the auxiliary memory device 23 stores notification contents in association with the determination result. The control unit 21 refers to the notification DB, acquires notification information according to the examination point and the determination result, and creates display screen information including the acquired notification information. The control unit 21 causes the display device 50 to display the display screen information including the created notification information. Further, the control unit 21 acquires the position information of the endoscope 40 on the basis of the examination point, and creates screen information indicating the current position.

FIG. 10 illustrates an example of a notification screen for notifying that the examination content has not been performed. The notification screen includes a text box including notification information and information of an illustration indicating the current position of the endoscope 40 in the body. When it is determined that an appropriate examination content has not been performed at the set examination point, a notification prompting the examiner to reconfirm is displayed. On the notification screen, a text "It has passed check point 02. Since capturing has not been performed, please check it again" or the like indicating the notification content is included. In a case where the endoscopic image 59 has not been acquired in a predetermined order or the endoscopic image 59 matching the examination point has not been acquired at the predetermined position, the control unit 21 determines that there is a possibility of omission of examination. In this case, the movement to the next examination point through the examination point can be prevented by displaying the notification prompting the reexamination.

FIG. 11 illustrates an example of a notification screen for notifying the reaching around the examination point. The notification screen includes a text box including notification information and information of an illustration indicating the current position of the endoscope 40 in the body. In a case where it is determined that the endoscope 40 has reached around the examination point, a notification indicating that the examination point is close is displayed. On the notification screen, a text "It is approaching check point 02. Please be careful not to omit the examination point" indicating the notification content is included. In the diagnostic support system 100, the examination point includes not only a check point but also the portion around the check point. For example, by setting the notification at the examination point close to the check point to be output, the notification for notifying the reaching at the portion around the check point is output, and the examination omission can be prevented.

Figure 12:
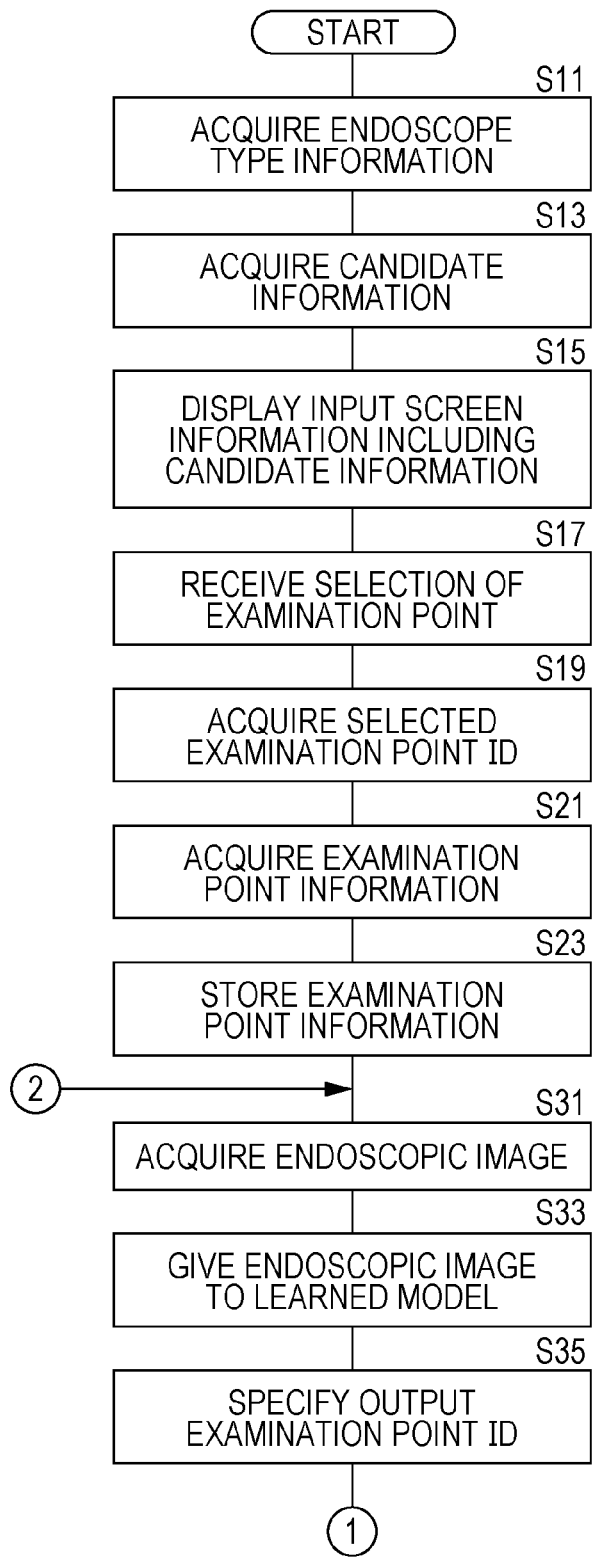
FIG. 12 is a flowchart illustrating an example of a processing procedure executed by the diagnostic support system.
Figure 13:
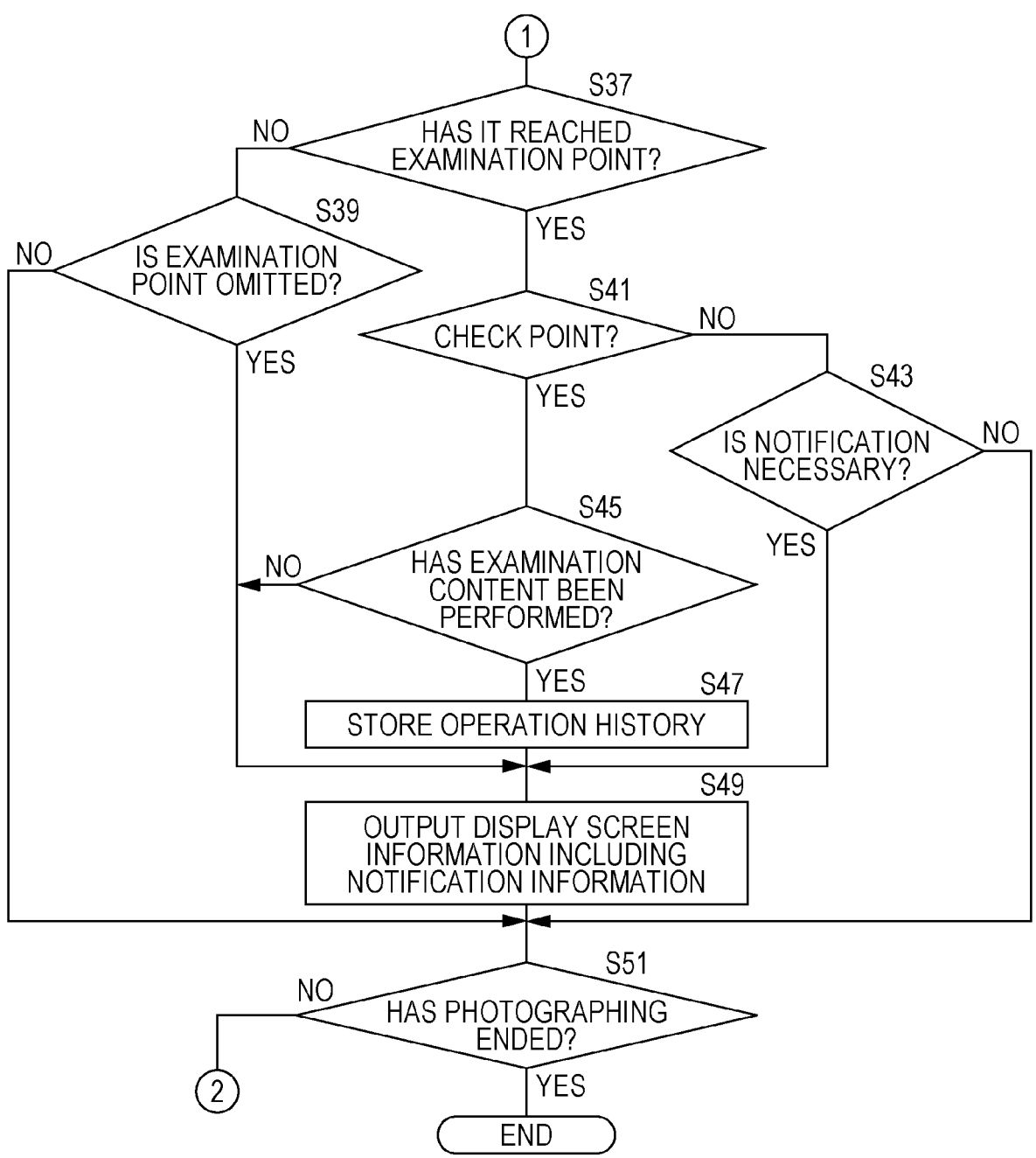
FIG. 13 is a flowchart illustrating an example of a processing procedure executed by the diagnostic support system.

FIGS. 12 and 13 are flowcharts illustrating an example of a processing procedure executed by the diagnostic support system 100. When the endoscope 40 is connected to the endoscope processor 20 and the program 231 of the endoscope processor 20 is activated, the control unit 21 executes the following processing. The control unit 21 executes the program illustrated in FIGS. 12 and 13 together with processing such as generation of the endoscopic image 59 and control of the light source 33 and the image sensor arranged at the distal tip 443 of the endoscope 40.

The control unit 21 acquires endoscope type information from the connected endoscope 40 (Step S11). The control unit 21 refers to the examination point DB 233 and acquires candidate information including the examination point corresponding to the type of the endoscope (Step S13). The candidate information includes information on a plurality of candidate check points. In order to receive the selection input of the examiner, the control unit 21 creates the input screen information including the candidate information and displays the input screen information on the display device 50 (Step S15).

The control unit 21 receives selection of the examination point (check point) by the examiner by an input operation of the keyboard 15, a mouse, or the like (Step S17), and acquires the examination point ID of the selected check point (Step S19). The control unit 21 refers to the examination point DB 233 and acquires examination point information corresponding to the examination content based on the selected check point (Step S21). The examination point information includes information on the examination point between the selected check point and the check point derived from the degree of relevance with the selected check point. The control unit 21 stores the acquired examination point information in the auxiliary memory device 23 (Step S23).

The endoscopic examination is started, and the endoscope 40 photographs an examination target portion. The control unit 21 acquires the endoscopic image 59 (Step S31). The control unit 21 gives the endoscopic image 59 to the learned model 237 (Step S33), and specifies the examination point ID to be output (Step S35). Note that the number of learned models 237 stored in the endoscope processor 20 is not limited to one, and a plurality of learned models according to the type of the endoscope may be prepared. In this case, the learned model according to the endoscope type information is selected. In addition, endoscope type information may be input as one of the elements of the input information.

The control unit 21 determines whether the distal tip 443 of the endoscope 40 has reached the examination point (Step S37). The control unit 21 refers to the auxiliary memory device 23 and determines whether the examination point ID of the examination point information selected and registered in advance matches the examination point ID corresponding to the endoscopic image 59 specified from the output value of the learned model 237.

When it is determined that the examination point IDs do not match or the examination point is not included in the endoscopic image 59 and thus the endoscope 40 has not reached the examination point selectively registered in advance (Step S37: NO), the control unit 21 then determines whether the examination point is omitted (Step S39). The control unit 21 determines whether the examination point is omitted based on the passing order, the position, and the like of the examination point included in the examination point information. When the endoscope 40 is moving to the next examination point, it is determined that the examination point is not omitted (Step S39: NO). In this case, the control unit 21 advances the processing to Step S51. On the other hand, when the endoscopic image 59 including the examination point ID is not acquired in a predetermined order, or when the endoscopic image 59 including the examination point ID is not acquired at a predetermined position, the control unit 21 determines that the examination point that has already passed is omitted (Step S39: YES), and the processing proceeds to Step S49.

When the examination point ID of the examination point information selected and registered in advance matches the examination point ID specified from the output value of the learned model 237, the control unit 21 determines that the endoscope 40 has reached the examination point (Step S37: YES). The control unit 21 determines whether the examination point is a check point on the basis of the examination point ID (Step S41).

In a case where the examination point included in the endoscopic image 59 is an examination point other than the check point (Step S41: NO), the control unit 21 determines whether to output a notification on the basis of the examination point information (Step S43). The control unit 21 refers to the information on the presence or absence of the output of the notification stored in the examination point information 234 of the examination point DB 233, and determines whether the examination point is an output target of the notification. When the examination point is not the output target of the notification, the control unit 21 determines not to output the notification (Step S43: NO), and advances the processing to Step S51. On the other hand, when the examination point is the output target of the notification, the control unit 21 determines that the output of the notification is necessary (Step S43: YES), and advances the processing to Step S49.

In a case where the examination point included in the endoscopic image 59 is a check point (Step S41: YES), the control unit 21 determines whether an appropriate examination content has been performed (Step S45). The control unit 21 determines whether imaging at the examination point has been performed, for example, by acquiring the presence or absence of the capture operation of the endoscope 40. When it is determined that the capture operation has been performed and an appropriate examination content has been performed (Step S45: YES), the control unit 21 stores an operation history of the endoscope 40 in the auxiliary memory device 23 (Step S47). On the other hand, when it is determined that the capture operation has not been performed and an appropriate examination content has not been performed (Step S45: NO), the control unit 21 advances the processing to Step S49.

In a case where various determination results regarding the examination at the examination point, such as the execution of an appropriate examination content by the endoscope 40, omission of the examination content, reaching around the examination point, or omission at the examination point, are acquired, the control unit 21 outputs a notification of the determination result. The control unit 21 acquires the determination result, and creates display screen information including notification information according to the determination result with reference to the notification DB. The control unit 21 outputs the display screen information including the created notification information to the display device 50 (Step S49). The notification information displayed on the display device 50 includes information regarding the examination content such as confirmation completion, omission of examination, and reaching around the examination point.

The control unit 21 determines whether photographing has not ended (Step S51). When it is determined that the photographing has not ended (Step S51: NO), the control unit 21 returns the processing to Step S31 and acquires a new endoscopic image. When it is determined that the photographing has ended (Step S51: YES), the control unit 21 ends a series of processing.

According to this embodiment, the examination content is detected in real time on the basis of the endoscopic image 59, and a notification corresponding to the detection result is output. Since the information regarding the implementation of the examination content is efficiently derived, the examiner can confirm the examination content based on the notification information.

Second Embodiment

Figure 14:
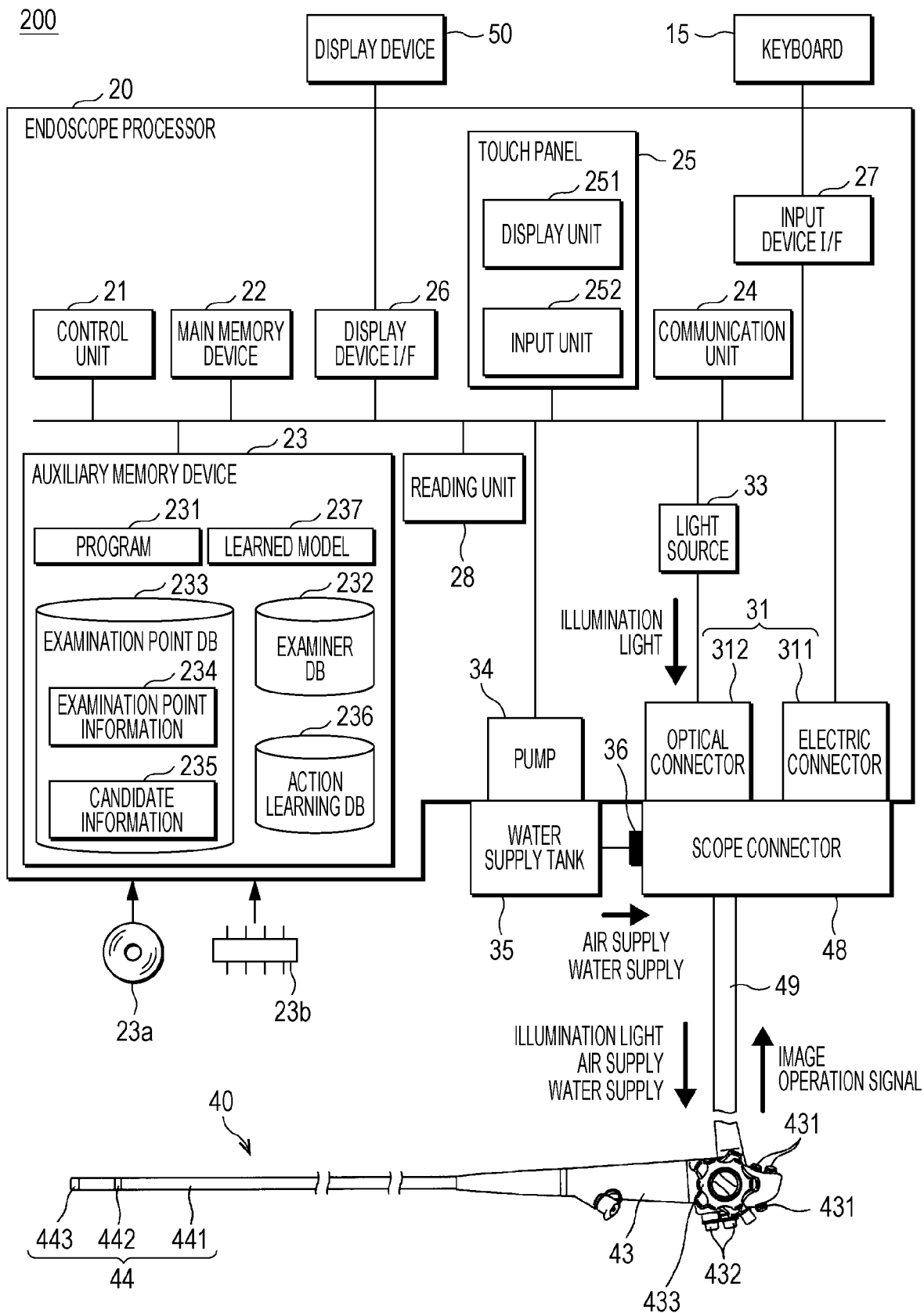
FIG. 14 is an explanatory diagram for explaining a configuration of a diagnostic support system according to a second embodiment.

The second embodiment is different from the first embodiment in that the endoscope processor 20 acquires motion information of an examiner and outputs a notification according to the skill level of the examiner. FIG. 14 is an explanatory diagram for explaining a configuration of a diagnostic support system 200 according to the second embodiment. Since a hardware configuration in the second embodiment is similar to that of the diagnostic support system 200 in the first embodiment, the same reference numerals are given to common configurations, and a detailed description thereof will be omitted. In the second embodiment, an action learning DB 236 is further stored in the auxiliary memory device 23 of the endoscope processor 20.

FIG. 15 is a diagram illustrating a content example of information stored in the action learning DB 236. The control unit 21 collects information regarding the operation of the endoscope 40 according to the endoscope type and the skill level, and stores the information in the action learning DB 236. The action learning DB 236 stores an endoscope type, a skill level, and motion information in association with a motion information ID for identifying motion information. The motion information is information indicating how the endoscope 40 operates at the time of examination with which a predetermined skill level is associated, and includes, for example, information such as a moving order and a moving time of the endoscope 40. The motion information may include, for example, image data, endoscope operation signal data, and the like. Detection of the motion information will be described later.

Figure 16:
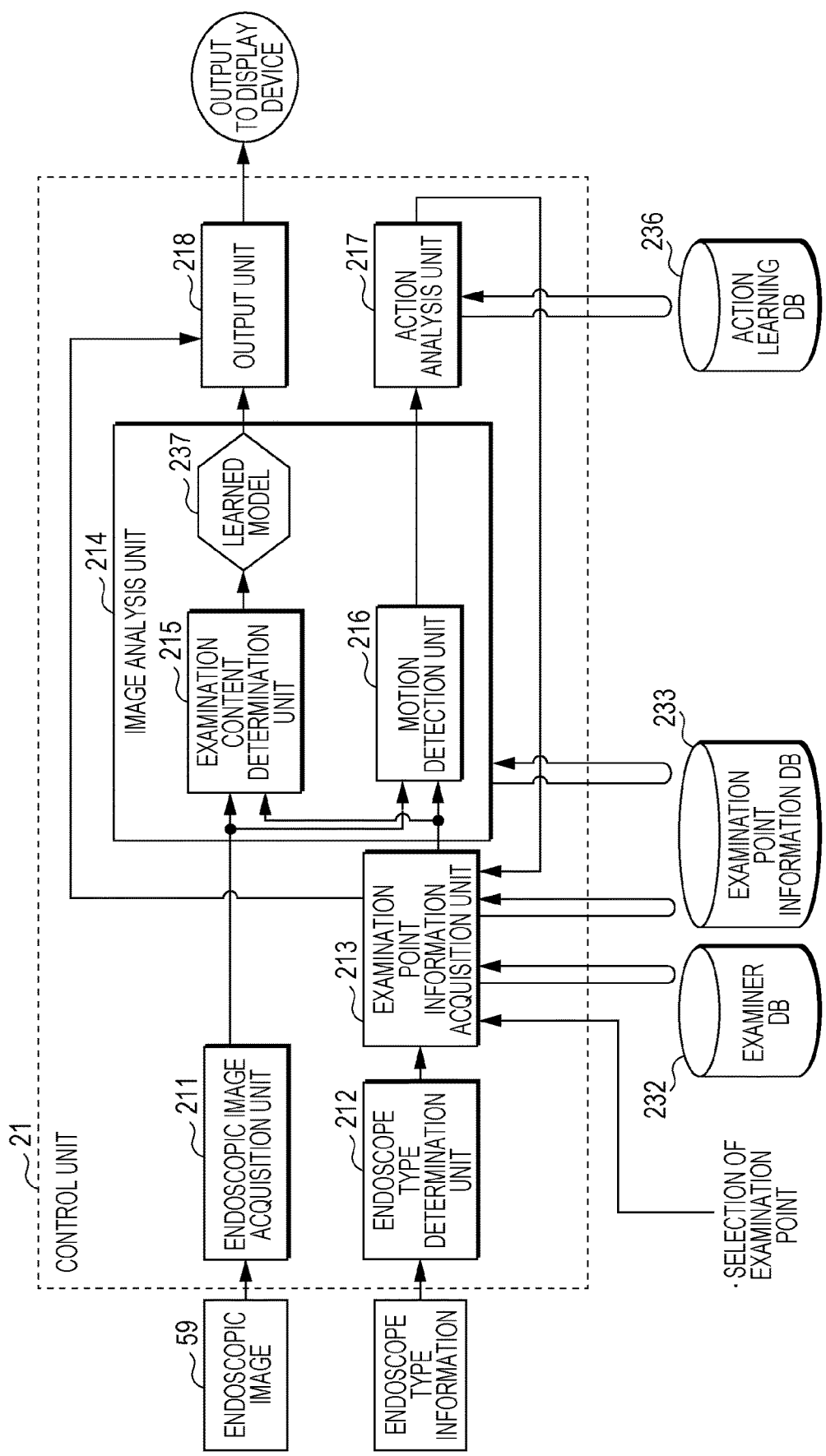
FIG. 16 is a functional block diagram illustrating functional units included in a control unit.

FIG. 16 is a functional block diagram illustrating functional units included in the control unit 21. In the second embodiment, the control unit 21 further includes a motion detection unit 216 and an action analysis unit 217 as functional units. The control unit 21 implements the functions of the motion detection unit 216 and the action analysis unit 217 by executing the program 231 stored in the auxiliary memory device 23.

In the second embodiment, the examination point information acquisition unit 213 acquires the examination point information according to the skill level of the examiner. The setting of the examination point may have different contents depending on the skill level of the examiner. For example, in a case where an examiner who is inexperienced in an endoscopic examination using a predetermined type of endoscope performs an examination, it is desirable to perform the examination by passing through all the basically set examination points without omission. On the other hand, in a case where a skilled examiner performs an examination, instead of performing the examination content at all the examination points which are basically set, the examination may be performed at the examination points in which several examination points are reduced. In addition, the examination point set according to the skill level may be changed. In the examiner DB 232, the target skill level of the examiner to include the examination point as the determination point is stored in association with the examination point information.

The examination point information acquisition unit 213 acquires the endoscope type information and the skill level of the examiner who performs the endoscopic examination. The examiner inputs an examiner ID and the like in advance on the input screen. The examination point information acquisition unit 213 acquires the examiner ID, and specifies the skill level associated with the examiner with reference to the examiner DB 232. The examination point information acquisition unit 213 refers to the examination point DB 233, extracts candidate information according to the endoscope type information and the target skill level, and displays a candidate check point included in the candidate information on the display device 50 via the output unit 218. The examiner selects or adds a check point from among the candidate check points displayed on the display device 50 according to the examination purpose, the skill level of the examiner, or the like, and sets the check point. The examination point information acquisition unit 213 receives an input of the keyboard 15, the mouse, or the like, and acquires the examination point ID of the selected check point.

The examination point information acquisition unit 213 specifies the examination point with reference to the examination point DB 233 based on the acquired examination point ID of the check point and the target skill level. In addition to the set check point, the examination point includes a portion around the check point added according to the skill level, a passing point between the check points, and the like. The examination point DB 233 stores the examination point in association with the target skill level. The examination point information acquisition unit 213 derives the examination point information associated with these examination points from the examination point DB 233. The examination point information acquisition unit 213 outputs the derived examination point information to the image analysis unit 214.

The image analysis unit 214 of the second embodiment includes the examination content determination unit 215 and the motion detection unit 216. The motion detection unit 216 performs image analysis of the endoscopic image 59 and detects the motion of the endoscope 40 at the time of examination. As a method of image analysis, for example, a known method such as pattern matching may be used.

Figure 17:
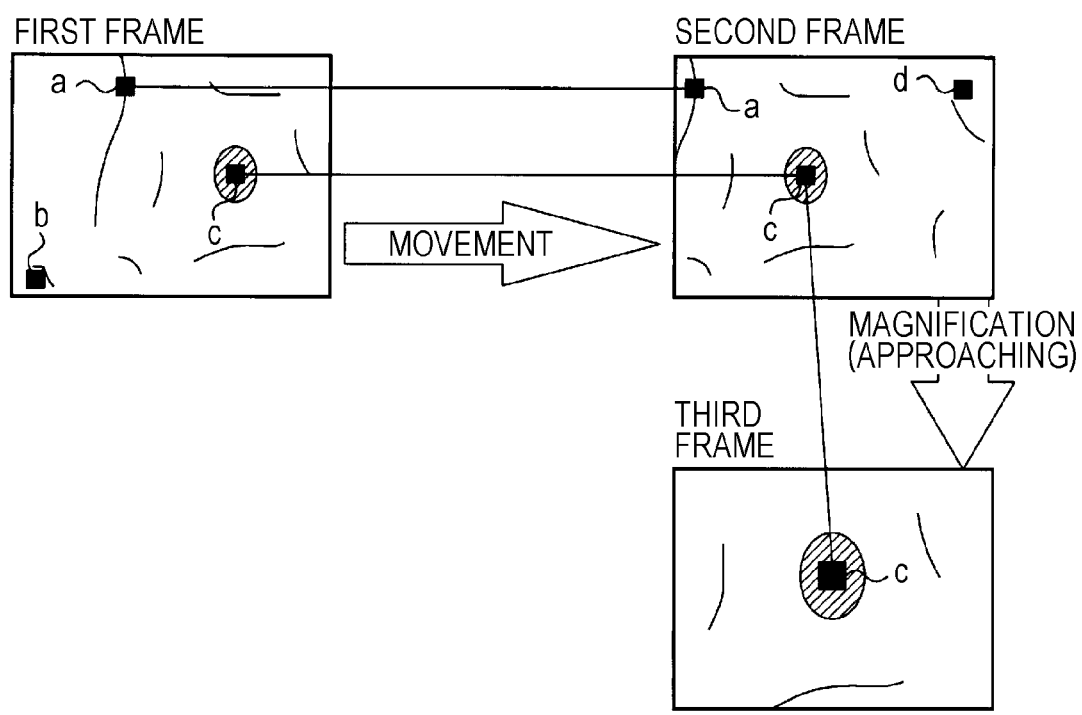
FIG. 17 is an explanatory diagram for explaining an example of motion detection.

FIG. 17 is an explanatory diagram illustrating an example of motion detection. The motion detection unit 216 extracts information such as the presence or absence, the position, and the size of the examination point in the imaging area of the endoscopic image 59 based on the feature amount of the endoscopic image 59 and the feature amount of the examination point stored in advance. Further, the motion detection unit 216 performs motion detection on the basis of image feature amounts of a plurality of frames of the endoscopic image 59.

FIG. 17 illustrates an example of a first frame, a second frame, and a third frame included in the endoscopic image 59. The motion detection unit 216 acquires frames of the endoscopic image 59 in the order of the first frame, the second frame, and the third frame. That is, the endoscope 40 moves the examination portion in the order of photographing in the first frame, the second frame, and the third frame. The motion detection unit 216 detects the motion of the endoscope by matching the image feature amount included in each frame. For example, the first frame includes a feature point a on the upper left side of the frame center, a feature point b on the lower left side, and a feature point c on the right side of the center. In the second frame, the feature point b disappears, the feature point a is included on the upper left side, the feature point c is included in the center, and the new feature point d is included on the upper right side. In the third frame, the feature point c is enlarged and displayed, and the feature point a and the feature point d disappear. Therefore, an operation indicating that the distal tip of the endoscope 40 has moved rightward is detected from the first frame and the second frame. In addition, an operation indicating that the distal tip 443 of the endoscope 40 has approached an attention region including the feature point b is detected from the second frame and the third frame. In this manner, the motion detection unit 216 detects the motion information. Note that the motion detection unit 216 may acquire an operation signal of the endoscope 40 and detect a motion on the basis of an operation history. In addition to the information regarding the movement path, the motion detection unit 216 detects information regarding the moving time required for movement between the examination points, between the passing points, and the like. The detected motion information is input to the action analysis unit 217.

The action analysis unit 217 performs an action analysis of the examiner with reference to the action learning DB 236 on the basis of the acquired motion information. The action analysis unit 217 evaluates the skill level of the examiner by the action analysis, and outputs an analysis result according to the skill level. For example, the action analysis unit 217 compares the acquired motion information of the examiner with the motion information associated with various skill levels included in the action learning DB 236. The action analysis unit 217 specifies a motion information ID having motion information with a high matching rate, and acquires a skill level associated with the motion information ID. The action analysis unit 217 specifies a skill level from the operation history of the endoscope 40, the time required for the operation, and the like on the basis of the motion information. For example, an examiner skilled in endoscopic examination can move the endoscope 40 from an examination point to an examination point in a short time without waste in the movement path of the endoscope 40.

The action analysis unit 217 compares the skill level obtained in real time from the analysis result with the skill level of the examiner acquired in advance, and determines whether to change the examination point. The action analysis unit 217 derives analysis result information including a determination result. The analysis result information is input to the examination point information acquisition unit 213. When it is necessary to change the examination point based on the acquired analysis result information, the examination point information acquisition unit 213 acquires the examination point information corresponding to the newly derived skill level.

Note that the action analysis unit 217 may determine the skill level of the examiner using another machine learning model. When the endoscopic image 59 is input, the action analysis unit 217 creates in advance a learned model that outputs information indicating the skill level and stores the learned model in the auxiliary memory device 23. The learned model is generated using data that collects endoscopic images at the time of examination by examiners of various skill levels. In a case where moving image data including a plurality of endoscopic images is input, the learned model outputs the skill level of the examiner estimated from the motion content obtained from the image information. The action analysis unit 217 acquires the information indicating the skill level from the endoscopic image 59 using the learned model. The information input to the learned model may include, for example, information such as an operation signal in addition to the endoscopic image 59.

Figure 18:
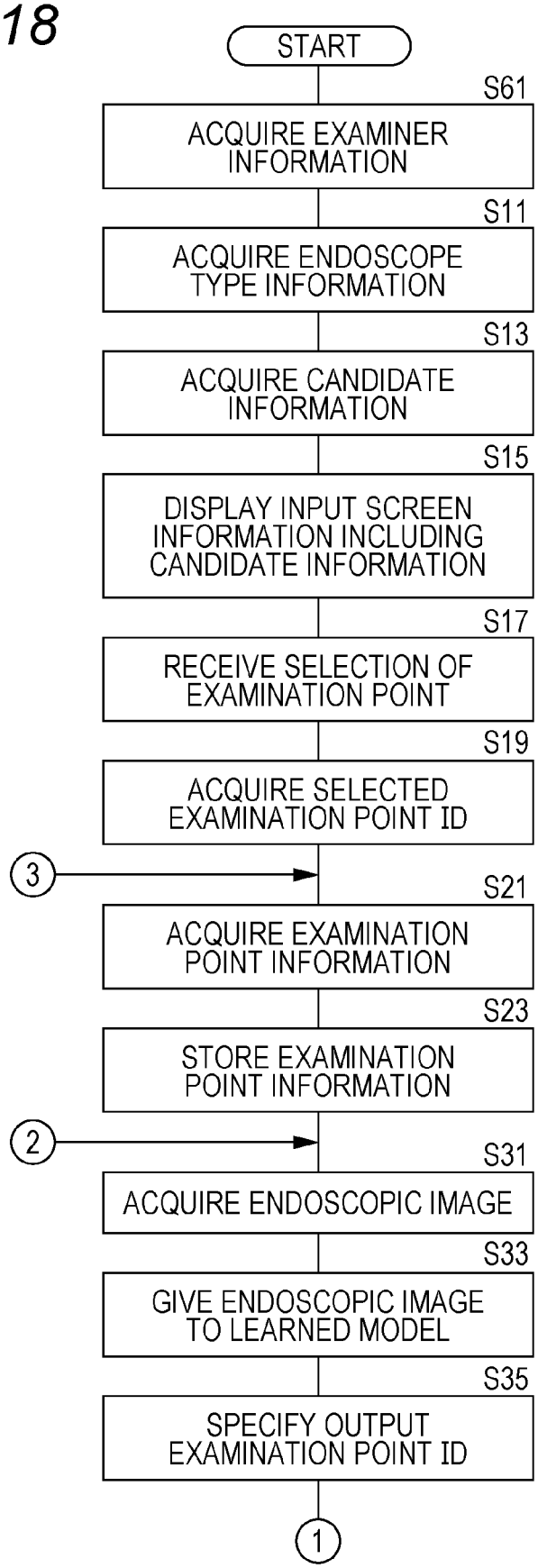
FIG. 18 is a flowchart illustrating an example of a processing procedure executed by the diagnostic support system.
Figure 19:
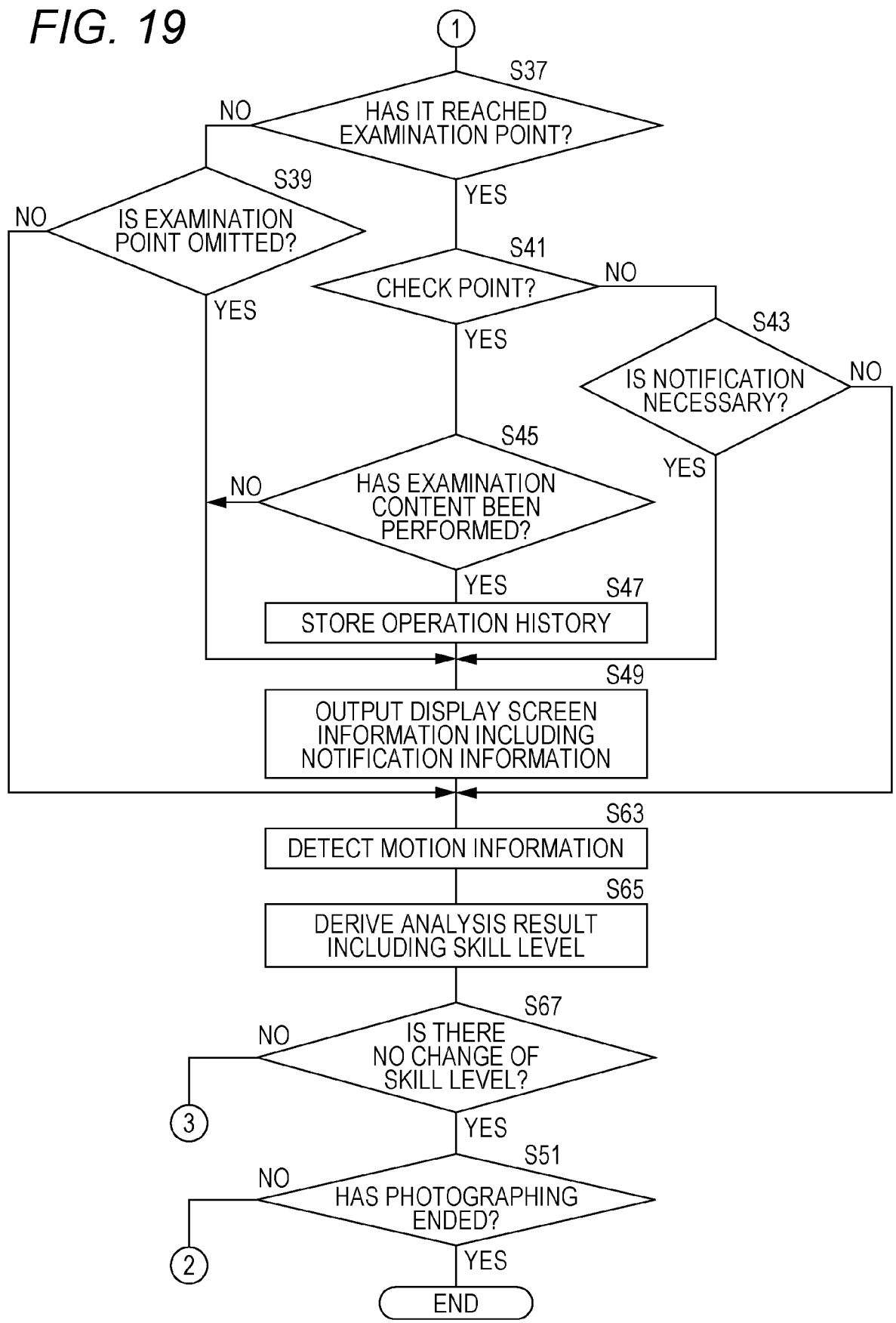
FIG. 19 is a flowchart illustrating an example of a processing procedure executed by the diagnostic support system.

FIGS. 18 and 19 are flowcharts illustrating an example of a processing procedure executed by the diagnostic support system 200. Processes in common with those in FIGS. 12 and 13 of the first embodiment are denoted by the same step numbers, and detailed descriptions thereof will be omitted. When the endoscope 40 is connected to the endoscope processor 20 and the program 231 of the endoscope processor 20 is activated, the control unit 21 executes the following processing.

The control unit 21 acquires examiner information of an examiner who performs an examination (Step S61). The control unit 21 receives an input operation from the keyboard 15, a mouse, or the like, and acquires an examiner ID. The control unit 21 refers to the examiner DB 232 to acquire examiner information including the skill level of the examiner.

The control unit 21 acquires endoscope type information (Step S11). The control unit 21 refers to the examination point DB 233 and acquires candidate information including a plurality of examination points according to the type of the endoscope and the skill level of the examiner (Step S13). The control unit 21 causes the display device 50 to display the input screen information including the candidate information (Step S15). Note that the control unit 21 may cause the display device 50 to display the candidate information based only on the endoscope type information regardless of the skill level.

The control unit 21 receives the selection of the examination point by the examiner (Step S17), and acquires the examination point ID of the selected check point (Step S19). The control unit 21 refers to the examination point DB 233 and acquires examination point information corresponding to the examination content based on the selected check point and skill level (Step S21). The examination point information includes examination point information such as a check point and a portion around the check point according to the skill level.

The endoscopic examination is started, and the endoscope 40 photographs an examination target portion. The control unit 21 performs the processing from Step S31 to Step S49 as in the first embodiment, and outputs a notification corresponding to the examination content. The examination point to be the output target of the notification varies depending on the skill level. For example, in a case where an untrained examiner performs an examination, not only a check point but also a portion around the check point is included in a notification output target. The notification is output in advance at the stage of reaching the vicinity of the check point, and the attention of the examiner is attracted so that the omission of the examination can be prevented. In a case where the skill level of the examiner is high, the notification before the check point is not output, and the notification is output only when the examination at the check point is completed.

Next, the control unit 21 detects motion information based on the endoscopic image 59 (Step S63). The control unit 21 detects motion information on the basis of image analysis of the endoscopic image 59, an operation signal, and the like. The control unit 21 performs action analysis with reference to the action learning DB 236 on the basis of the detected motion information. The control unit 21 specifies the skill level of the examiner reflecting the motion information in real time by the action analysis. The control unit 21 derives an analysis result including the specified skill level (Step S65).

The control unit 21 acquires information of whether to change the skill level of the examiner on the basis of the analysis result (Step S67). If the skill level included in the examiner information acquired in advance is different from the skill level included in the analysis result, or if the difference in skill level is equal to or greater than a threshold (Step S67: NO), the control unit 21 determines to change the skill level. The control unit 21 returns the processing to Step S21, and acquires examination point information based on the newly derived skill level. For example, in a case where the skill level is changed to a low numerical value, the examination point information is changed so that a notification is output to a portion around the check point in addition to the check point. On the other hand, when the skill level included in the examiner information acquired in advance is the same as the skill level included in the analysis result, or when the difference in skill level is less than the threshold (Step S67: YES), the control unit 21 determines not to change the skill level and advances the processing to the next Step S51.

The control unit 21 determines whether photographing has ended (Step S51). When it is determined that the photographing has not ended (Step S51: NO), the control unit 21 returns the processing to Step S31 and acquires a new endoscopic image. When it is determined that the photographing has ended (Step S51: YES), the control unit 21 ends a series of processing.

According to this embodiment, the notification regarding the examination content is output on the basis of the result of the action analysis performed in real time. Since the information regarding the implementation of the examination content is efficiently derived, it is possible to provide information according to the examination content of the examiner.

The embodiments disclosed as described above should be considered to be exemplary in all respects without being limited. The technical features described in the embodiments can be combined with each other, and the scope of the present invention is intended to include all modifications within the scope of the claims and the scope equivalent to the claims.

REFERENCE SIGNS LIST

20 endoscope processor
21 control unit
211 endoscopic image acquisition unit
212 endoscope type determination unit
213 examination point information acquisition unit
214 image analysis unit
215 examination content determination unit
216 motion detection unit
217 action analysis unit
218 output unit
23 auxiliary memory device
231 program
232 examiner DB
233 examination point DB
234 examination point information
235 candidate information
236 action learning DB
237 learned model
40 endoscope
50 display device
59 endoscopic image
100, 200 diagnostic support system

The invention claimed is:

1. A computer program for causing a computer to execute:
   acquiring examination point information regarding an examination point included in an examination target portion using an endoscope, wherein the examination point information includes an examination point ID, identifying by alphanumeric symbols the acquired examination point information and manually inputted by an examiner;
   acquiring an endoscopic image captured by the endoscope;
   determining whether the endoscope has reached the examination point on the basis of image analysis of the acquired endoscopic image that includes using the alphanumeric symbols of the examination point ID in determining whether the examination point of the examination point information matches an examination point determined from the analysis of the acquired endoscope image;
   outputting a notification when the endoscope has reached the examination point; and
   acquiring motion information of the an examiner who performs an examination at the examination point on the basis of the endoscopic image or an operation signal of the endoscope.

2. The computer program according to claim 1, wherein the notification includes information regarding an examination content at the examination point.

3. The computer program according to claim 1, further executing:
   acquiring the examination point by inputting the endoscopic image to a learned model that outputs the examination point corresponding to the endoscopic image when the endoscopic image is input; and
   determining whether the endoscope has reached the examination point based on the acquired examination point and the acquired examination point information regarding the examination point.

4. The computer program according to claim 1, wherein the notification outputting outputs the notification when a predetermined examination content is not performed at the examination point.

5. The computer program according to claim 1, for further executing:
   acquiring a skill level of the examiner performing the examination with respect to the examination; and
   changing a content of the notification on the basis of the acquired skill level.

6. The computer program according to claim 1, for further executing:
   deriving a skill level of the examiner with respect to the examination according to an execution content of the examination based on the acquired motion information.

7. The computer program according to claim 6, for further executing:

acquiring the examination point information on the basis of the derived skill level with respect to the examination corresponding to the execution content of the examination.

8. The computer program according to claim 1, for further executing:
displaying a plurality of candidates of examination point information stored in advance; and
receiving selection from the examiner who performs the examination, and determining the examination point information corresponding to the examination.

9. The computer program according to claim 1, for further executing:
specifying a type of the endoscope used for the examination; and
acquiring the examination point information corresponding to the specified type of the endoscope.

10. The computer program according to claim 1, wherein the examination point information includes
   a) the examination point ID,
   b) a check point,
   c) an examination point position,
   d) an examination point image,
   e) the type of endoscope,
   f) notification information on whether a notification is output to the examiner at the examination point, and
   g) a target skill level of the examiner,
the user-inputted alphanumeric symbols of the examination point ID identify the check point, the examination point position, the image, the type of endoscope, the notification information, and the target skill level of the examiner contained in the examination point information, and
the computer program causes the computer to retrieve the check point, the examination point position, the image, the type of endoscope, the notification information, and the target skill level of the examiner contained in the examination point information in response to inputting of the user-inputted alphanumeric symbols of the examination point ID.

11. The computer program according to claim 10, wherein the examination point information is stored in an examination point database of the computer, and
the examination point database stores, in association with each other:
   a) the examination point ID;
   b) the check point;
   c) the examination point position;
   d) the examination point image;
   e) the type of endoscope;
   f) the notification information on whether a notification is output to the examiner at the examination point; and
   g) the target skill level of the examiner.

12. The computer program according to claim 1, wherein the computer includes an examination point database storing
   plural endoscope-type data identifying different endoscope types imaging different body parts,
   the examination point information about the examination point,
   additional examination point information about additional examination points, and
   plural examination point IDs, each for a different examination point of different examination point information, the examination point database associates data for each endoscope type with a plurality of corresponding examination point IDs, and
the computer program causes the computer to retrieve a plurality of corresponding examination point IDs for each type of endoscope, thereby retrieving a plurality of alphanumeric symbols identifying a plurality of candidate examination points for each endoscope type.

13. A processor for an endoscope, comprising:
an examination point information acquisition unit that acquires examination point information regarding an examination point included in an examination target portion using an endoscope, wherein the examination point information includes an examination point ID, identifying by alphanumeric symbols the acquired examination point information and manually inputted by an examiner;
an endoscopic image acquisition unit that acquires an endoscopic image captured by the endoscope;
a determination unit that determines whether the endoscope has reached the examination point on the basis of image analysis of the acquired endoscopic image that includes using the alphanumeric symbols of the examination point ID in determining whether the examination point of the examination point information matches an examination point determined from the analysis of the acquired endoscope image;
an output unit that outputs a notification when the endoscope has reached the examination point; and
an acquiring unit that acquires motion information of an examiner who performs an examination at the examination point on the basis of the endoscopic image or an operation signal of the endoscope.

14. The processor for an endoscope according to claim 13, wherein the determination unit inputs the endoscopic image to a learned model that outputs the examination point corresponding to the endoscopic image when the endoscopic image is input, and acquires the examination point to be output, and
wherein the determination unit determines whether the endoscope has reached the examination point based on the acquired examination point and the acquired examination point information regarding the examination point.

15. The processor according to claim 13, wherein the examination point information includes
   a) the examination point ID,
   b) a check point,
   c) an examination point position,
   d) an examination point image,
   e) the type of endoscope,
   f) notification information on whether a notification is output to the examiner at the examination point, and
   g) a target skill level of the examiner,
the user-inputted alphanumeric symbols of the examination point ID identify the check point, the examination point position, the image, the type of endoscope, the notification information, and the target skill level of the examiner contained in the examination point information, and
the processor retrieves the check point, the examination point position, the image, the type of endoscope, the notification information, and the target skill level of the examiner contained in the examination point information in response to inputting of the user-inputted alphanumeric symbols of the examination point ID.

16. The processor according to claim 15, wherein
the examination point information is stored in an examination point database of the computer, and
the examination point database stores, in association with each other:
  a) the examination point ID;
  b) the check point;
  c) the examination point position;
  d) the examination point image;
  e) the type of endoscope;
  f) the notification information on whether a notification is output to the examiner at the examination point; and
  g) the target skill level of the examiner.

17. The processor according to claim 13, wherein
the processor accesses an examination point database storing
  plural endoscope-type data identifying different endoscope types imaging different body parts,
    the examination point information about the examination point,
    additional examination point information about additional examination points, and
    plural examination point IDs, each for a different examination point of different examination point information,
the examination point database associates data for each endoscope type with a plurality of corresponding examination point IDs, and
the processor retrieves a plurality of corresponding examination point IDs for each type of endoscope, thereby retrieving a plurality of alphanumeric symbols identifying a plurality of candidate examination points for each endoscope type.

18. An information processing method, comprising:
acquiring examination point information regarding an examination point included in an examination target portion using an endoscope, wherein the examination point information includes an examination point ID, identifying by alphanumeric symbols the acquired examination point information and manually inputted by an examiner;
acquiring an endoscopic image captured by the endoscope;
determining whether the endoscope has reached the examination point on the basis of image analysis of the acquired endoscopic image that includes using the alphanumeric symbols of the examination point ID in determining whether the examination point of the examination point information matches an examination point determined from the image analysis of the acquired endoscope image;
outputting a notification when the endoscope has reached the examination point; and
acquiring motion information of an examiner who performs an examination at the examination point on the basis of the endoscopic image or an operation signal of the endoscope.

* * * * *